US009284612B2

(12) United States Patent
Liao et al.

(10) Patent No.: US 9,284,612 B2
(45) Date of Patent: Mar. 15, 2016

(54) FERMENTIVE PRODUCTION OF ISOBUTANOL USING HIGHLY ACTIVE KETOL-ACID REDUCTOISOMERASE ENZYMES

(75) Inventors: Der-Ing Liao, Wilmington, DE (US); Mark J. Nelson, Newark, DE (US); Michael G. Bramucci, Boothwyn, PA (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days.

(21) Appl. No.: 13/031,776

(22) Filed: Feb. 22, 2011

(65) Prior Publication Data

US 2011/0250610 A1    Oct. 13, 2011

Related U.S. Application Data

(63) Continuation of application No. 12/103,844, filed on Apr. 16, 2008, now Pat. No. 7,910,342.

(60) Provisional application No. 60/912,491, filed on Apr. 18, 2007.

(51) Int. Cl.
| C12N 9/00 | (2006.01) |
| C12Q 1/68 | (2006.01) |
| C12N 9/04 | (2006.01) |
| C12P 7/42 | (2006.01) |

(52) U.S. Cl.
CPC .............. *C12Q 1/689* (2013.01); *C12N 9/0006* (2013.01); *C12P 7/42* (2013.01)

(58) Field of Classification Search
None
See application file for complete search history.

(56) References Cited

U.S. PATENT DOCUMENTS

| 4,683,202 | A  | 7/1987  | Mullis et al. |
| 4,865,973 | A  | 9/1989  | Kollerup et al. |
| 5,643,779 | A  | 7/1997  | Erlich et al. |
| 6,586,229 | B1 | 7/2003  | Ben-Bassat et al. |
| 7,541,173 | B2 | 6/2009  | Bramucci et al. |
| 7,659,104 | B2 | 2/2010  | Bramucci et al. |
| 7,851,188 | B2 | 12/2010 | Donaldson et al. |
| 7,910,342 | B2 | 3/2011  | Liao et al. |
| 7,993,889 | B1 | 8/2011  | Donaldson et al. |
| 8,017,364 | B2 | 9/2011  | Bramucci et al. |
| 8,071,358 | B1 | 12/2011 | Dundon et al. |
| 8,129,162 | B2 | 3/2012  | Li et al. |
| 8,178,328 | B2 | 5/2012  | Donaldson et al. |
| 8,188,250 | B2 | 5/2012  | Bramucci et al. |
| 8,206,970 | B2 | 6/2012  | Eliot et al. |
| 8,222,017 | B2 | 7/2012  | Li et al. |
| 8,241,878 | B2 | 8/2012  | Anthony et al. |
| 8,273,558 | B2 | 9/2012  | Donaldson et al. |
| 8,283,144 | B2 | 10/2012 | Donaldson et al. |
| 8,372,612 | B2 | 2/2013  | Larossa et al. |
| 8,389,252 | B2 | 3/2013  | Larossa |
| 8,455,224 | B2 | 6/2013  | Paul |
| 8,455,225 | B2 | 6/2013  | Bramucci et al. |
| 8,465,964 | B2 | 6/2013  | Anthony et al. |
| 8,518,678 | B2 | 8/2013  | Flint et al. |
| 8,557,562 | B2 | 10/2013 | Bramucci et al. |
| 8,614,085 | B2 | 12/2013 | Van Dyk et al. |
| 8,637,281 | B2 | 1/2014  | Paul et al. |
| 8,637,289 | B2 | 1/2014  | Anthony et al. |
| 8,652,823 | B2 | 2/2014  | Flint et al. |
| 8,669,094 | B2 | 3/2014  | Anthony et al. |
| 8,691,540 | B2 | 4/2014  | Bramucci et al. |
| 8,735,114 | B2 | 5/2014  | Donaldson et al. |
| 8,765,433 | B2 | 7/2014  | Gude et al. |
| 8,785,166 | B2 | 7/2014  | Anthony et al. |
| 8,795,992 | B2 | 8/2014  | Bramucci et al. |
| 8,828,694 | B2 | 9/2014  | Anthony et al. |
| 8,828,704 | B2 | 9/2014  | Donaldson et al. |
| 8,871,488 | B2 | 10/2014 | Dauner et al. |
| 8,889,385 | B2 | 11/2014 | Donaldson et al. |
| 8,895,307 | B2 | 11/2014 | Li et al. |
| 8,906,666 | B2 | 12/2014 | Alsaker |
| 8,911,981 | B2 | 12/2014 | Li et al. |
| 8,940,511 | B2 | 1/2015  | Larossa |
| 8,945,859 | B2 | 2/2015  | Donaldson et al. |
| 8,945,899 | B2 | 2/2015  | Li et al. |
| 8,951,774 | B2 | 2/2015  | Donaldson et al. |
| 8,951,937 | B2 | 2/2015  | Flint et al. |
| 8,956,850 | B2 | 2/2015  | Anthony et al. |
| 8,962,298 | B2 | 2/2015  | Donaldson et al. |
| 8,969,065 | B2 | 3/2015  | Anthony et al. |
| 8,980,612 | B2 | 3/2015  | Donaldson et al. |
| 2002/0061569 | A1 | 5/2002 | Haselbeck et al. |
| 2004/0234649 | A1 | 11/2004 | Lewis et al. |
| 2004/0248250 | A1 | 12/2004 | Nakai et al. |

(Continued)

FOREIGN PATENT DOCUMENTS

| WO | WO9408020 | 4/1994 |
| WO | WO0112833 | * 2/2001 ................ C12P 7/00 |

(Continued)

OTHER PUBLICATIONS

Butanols, Ullman'S Encyclopedia of Industrial Chemistry, 6th Edition, 2003, vol. 5:716-719.
Carlini et al., Guerbet Condensation of Methanol With N-Propanol to Isobutyl Alcohol Over Heterogeneous Copper Chromite/Mg—Al Mixed Oxides Catalysts, J. Molec. Catal. A: Chem., 2004, vol. 220:215-220.
Dickinson et al., An Investigation of the Metabolism of Valine to Isobutyl Alcohol in *Saccharomyces cerevisiae*, J. Biol. Chem., 1998, vol. 273:25752-25756.
Garcia et al., Fusel Alcohols Production in Beer Fermentation Processes, Process Biochemistry, 1994, vol. 29:303-309.
Oaxaca et al., Formation of Ethanol and Higher Alcohols by Immobilized Zymomonas Mobilis in Continuous Culture, Acta Biotechnol., 1991, vol. 11:523-532.

(Continued)

*Primary Examiner* — Michele K Joike

(57) ABSTRACT

Methods for the fermentative production of isobutanol is provided by the fermentative growth of a recombinant microorganism expressing a highly active ketol-acid reductoisomerase enzyme in addition to other enzymes required for conversion of glucose to isobutanol.

5 Claims, 2 Drawing Sheets

(56) References Cited

U.S. PATENT DOCUMENTS

Figure 1A:
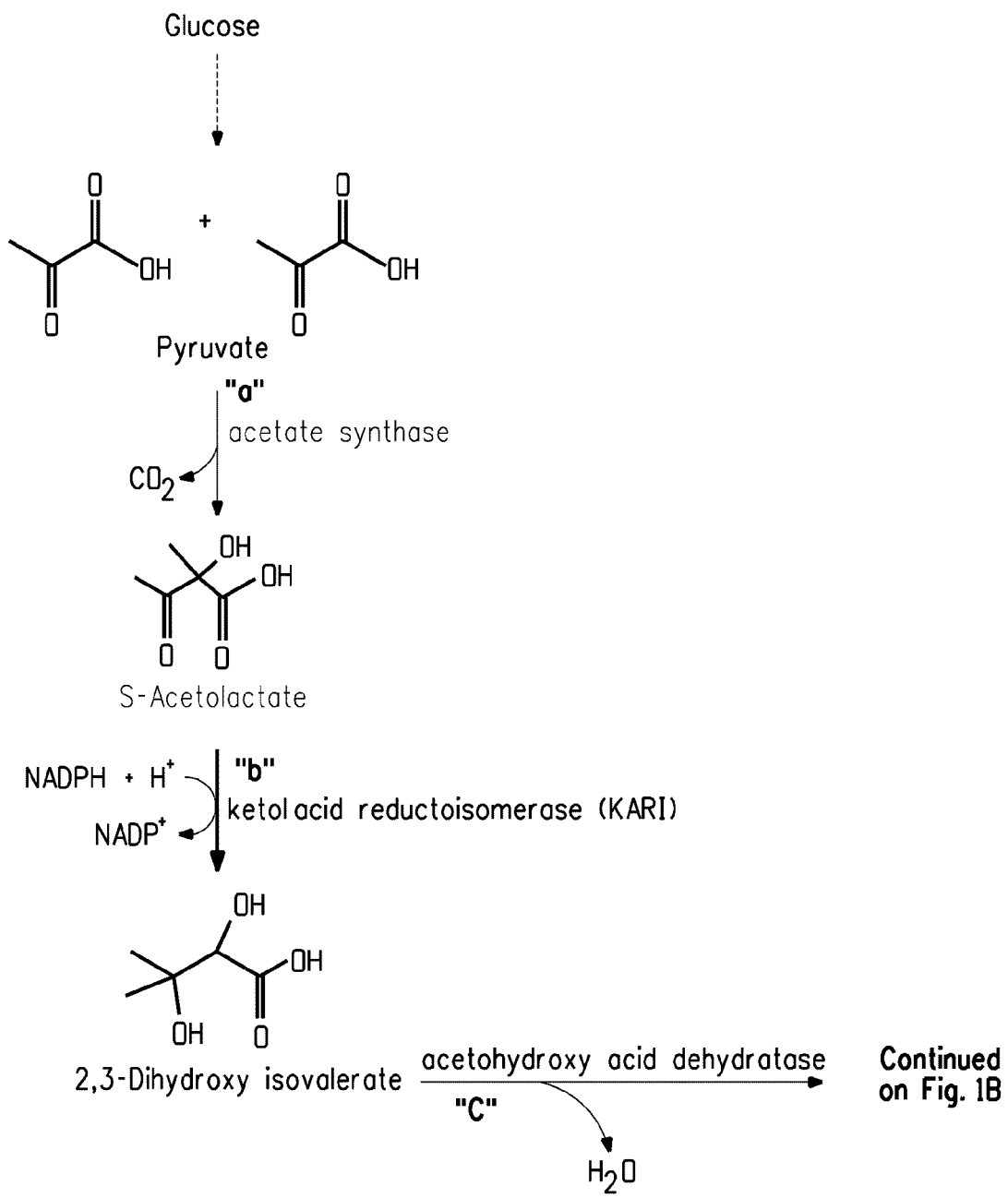

| | | | |
|---|---|---|---|
| 2005/0112739 A1 | 5/2005 | Golubkov et al. | |
| 2007/0031918 A1 | 2/2007 | Dunson et al. | |
| 2007/0092957 A1 | 4/2007 | Donaldson et al. | |
| 2007/0259411 A1* | 11/2007 | Bramucci et al. | 435/160 |
| 2008/0182308 A1 | 7/2008 | Donaldson et al. | |
| 2009/0081746 A1 | 3/2009 | Liao | |
| 2010/0081154 A1 | 4/2010 | Flint et al. | |
| 2010/0081179 A1 | 4/2010 | Anthony et al. | |
| 2010/0081182 A1 | 4/2010 | Paul et al. | |
| 2010/0093020 A1 | 4/2010 | Bramucci et al. | |
| 2010/0120105 A1 | 5/2010 | Anthony et al. | |
| 2010/0143997 A1 | 6/2010 | Buelter et al. | |
| 2011/0076733 A1 | 3/2011 | Urano et al. | |
| 2011/0111472 A1* | 5/2011 | Donaldson et al. | 435/160 |
| 2011/0124060 A1 | 5/2011 | Anthony et al. | |
| 2011/0136192 A1 | 6/2011 | Paul et al. | |
| 2011/0195505 A1 | 8/2011 | Euler et al. | |
| 2011/0244536 A1 | 10/2011 | Nagarajan et al. | |
| 2011/0275129 A1 | 11/2011 | Buelter et al. | |
| 2012/0058541 A1 | 3/2012 | Alsaker et al. | |
| 2012/0064561 A1 | 3/2012 | Flint et al. | |
| 2012/0149080 A1 | 6/2012 | Bramucci et al. | |
| 2012/0196341 A1 | 8/2012 | Donaldson et al. | |
| 2012/0237988 A1 | 9/2012 | Anthony et al. | |
| 2012/0258873 A1 | 10/2012 | Gibson et al. | |
| 2013/0035515 A1 | 2/2013 | Dobson et al. | |
| 2013/0071898 A1 | 3/2013 | Anthony et al. | |
| 2013/0171706 A1 | 7/2013 | Donaldson et al. | |
| 2013/0203138 A1 | 8/2013 | McElvain et al. | |
| 2013/0252296 A1 | 9/2013 | Maggio-Hall et al. | |
| 2013/0316414 A1 | 11/2013 | Paul et al. | |
| 2014/0004526 A1 | 1/2014 | Dauner et al. | |
| 2014/0030782 A1 | 1/2014 | Anthony et al. | |
| 2014/0030783 A1 | 1/2014 | Anthony et al. | |
| 2014/0038263 A1 | 2/2014 | Flint et al. | |
| 2014/0038268 A1 | 2/2014 | Flint et al. | |
| 2014/0051133 A1 | 2/2014 | Govindarajan et al. | |
| 2014/0051137 A1 | 2/2014 | Flint et al. | |
| 2014/0057329 A1 | 2/2014 | Li et al. | |
| 2014/0093930 A1 | 4/2014 | Li et al. | |
| 2014/0096439 A1 | 4/2014 | Bramucci et al. | |
| 2014/0141479 A1 | 5/2014 | Anthony et al. | |
| 2014/0170732 A1 | 6/2014 | Bramucci et al. | |
| 2014/0186910 A1 | 7/2014 | Rothman et al. | |
| 2014/0186911 A1 | 7/2014 | Anthony et al. | |
| 2014/0273116 A1 | 9/2014 | Kelly et al. | |
| 2014/0273129 A1 | 9/2014 | Bhalla et al. | |
| 2014/0308735 A1 | 10/2014 | Anthony et al. | |
| 2014/0335582 A1 | 11/2014 | Donaldson et al. | |
| 2014/0349349 A1 | 11/2014 | Dauner et al. | |
| 2014/0377824 A1 | 12/2014 | Satagopan et al. | |
| 2015/0037855 A1 | 2/2015 | Bhadra et al. | |
| 2015/0111269 A1 | 4/2015 | Li et al. | |

FOREIGN PATENT DOCUMENTS

| | | |
|---|---|---|
| WO | 0170955 A2 | 9/2001 |
| WO | 2005040392 A1 | 5/2005 |
| WO | 2008098227 A2 | 8/2008 |
| WO | WO2008130995 | 10/2008 |
| WO | WO2009056984 | 5/2009 |
| WO | WO2009059253 | 5/2009 |
| WO | WO2009078108 | 6/2009 |
| WO | WO2009086423 | 7/2009 |
| WO | WO2010051527 | 5/2010 |
| WO | WO2010062597 | 6/2010 |
| WO | WO2011019894 | 2/2011 |

OTHER PUBLICATIONS

S. Epelbaum et al., Branched-Chain Amino Acid Biosynthesis in *Salmonella typhimurium*: A Quantitative Analysis, J. Bacteriol., 1998, vol. 180:4056-4067.
R. Tyagi et al., The Crystal Structure of a Bacterial Class II Ketol-Acid Reductoisomerase: Domain Conservation and Evolution, Protein Science, 2005, vol. 14:3089-3100.
H. Ahn et al., Crystal Structure of Class I Acetohydroxy Acid Isomeroreductase From Pseudomonas Aeruginosa, Journal of Molecular Biology, 2003, vol. 328:505-515.
A. Aulabaugh et al., Oxalyl Hydroxamates As Reaction-Intermediate Analogues for Ketol-Acid Reductoisomerase, Biochemistry, 1990, vol. 29:2824-2830.
M. Rane et al., Reversal of the Nucleotide Specificity of Ketol Acid Reductoisomerase by Site-Directed Mutagenesis Identifies the NADPH Binding Site, Archives of Biochemistry and Biophysics, Feb. 1, 1997, vol. 338, No. 1, pp. 83-89.
NCBI Accession No. NC_000913, Region: 3955993..3957468, *Escherichia coli*; May 17, 2008.
NCBI Accession No. NC_002505, Region: 157441..158925, Vibrio Cholerae, Jul. 21, 2008.
NCBI Accession No. NC_002516, Region: 5272455..5273471, Pseudomonas Aeruginosa, Jul. 20, 2008.
NCBI Accession No. NC_004129, Region: 6017379.. 6018395, Pseudomonas Fluorescens, Jul. 20, 2008.
Kuzuyama, Mevalonate and Nonmevalonate Pathways for the Biosynthesis of Isoprene Units, Biosci. Biotechnol. Biochem., 2002, pp. 1619-1627, vol. 66, No. 8.
Heidelberg, J. et al., Database GENESEQ, Database Accession No. A3EGY6, Mar. 20, 2007.
Haselbeck, R. et al., Database GENESEQ, Database Accession No. AAU36450, Feb. 14, 2002.
Paulsen, I. T., et al., Database GENESEQ, Database Accession No. Q4K608, Aug. 2, 2005.
Paulsen, I. T., et al., Complete genome sequence of the plant commensal Pseudomonas fluorescens Pf-5, Nature Biotechnology, Jul. 2005, pp. 873-878, vol. 23, No. 7 Complete Genome Sequence of the Plant Commensal Pseudomonas FL.
International Search Report dated Dec. 12, 2008, International Application No. PCT/US2008/060466.
International Preliminary Report on Patentability in corresponding PCT/US2008/060466 mailed on Oct. 29, 2009.
Durner et al., Ketol-Acid Reductoisomerase From Barley (*Hordeum vulgare*) (Purification, Properties, and Specific Inhibition) Plantphysiol. 1993, 103(3), 903-910.
Spano et al., Environmental Stress Response in Wine Lactic Acid Bacteria: Beyond Bacillus subtilis, Crit. Rev. Microbiol., 2006 32(2), 77-86.
Abbad-Andaloussi, et al., Carbon and Electron FLow in Clostridium butyricum grown in Chemostat Culture on Glycerol and on Glucose, Microbiology 142:1149-1158, 1996.
Arthur, et al., Contribution of VanY D,D-Carboxypeptidase to Glycopeptide Resistance in Enterococcus faecalis by Hydrolysis of Peptidoglycan Precursor, Antimicrob. Agents Chemother. 38:1899-1903, 1994.
Vasantha, et al., Genes for Alkaline Protease and Neutral Protease from Bacillus amyloliquefaciens Contain a Large Open Reading Frame Between the Regions Coding for Signal Sequence and Mature Protein, J. Bacteriol., 159:811-819, 1984.
Biou, et al. The crystal structure of plant acetohydroxy acid isomeroreductase complexed with NADPH, two magnesium ions and a herbicidal transition state analog determined at 1.65 Å resolution, EMBO Journal 16:3405-3415, 1997.
van der Geize, et al., Targeted Disruption of the kstD Gene Encoding a 3-Ketosteroid delta1-Dehydrogenase Isoenzyme of Rhodococcus erythropolis Strain SQ1, Appl. Environ. Microbiol. 66:2029-2036, 2000.
Chunduru, et al., Mechanism of Ketol Acid Reductoisomerase—Steady State Analysis and Metal Ion Requirement, Biochemistry 28:486-493 1989.
de Cavalho, et al., *Mycobacterium* sp., *Rhodococcus erythropolis*, and *Pseudomonas putida* Behavior in the Presence of Organic Solvents, Microsc. Res. Tech. 64:215-22, 2004.
de la Plaza, et al., Biochemical and molecular characterization of alpha-ketoisovalerate decarboxylase, an enzyme involved in the formation of aldehydes from amino acids by Lactococcus lactis, FEMS Microbiol. Lett. 238:367-374, 2004.
Deshpande, Ethanol Production from Cellulose by Coupled Saccharification/Fermentation using *Saccharomyces cerevisiae* and Cel-

(56) References Cited

OTHER PUBLICATIONS lulase Complex from Sclerotium rolfsii UV-8 Mutant, Appl. Biochem. Biotechnol. 36:227, 1992.

Dürre, et al., Solventogenic Enzymes of Clostridium acetobutylicum: Catalytic Properties, Genetic Organization, and Transcriptional Regulation, FEMS Microbiol. Rev. 17:251-262, 1995.

Dürre, New insights and novel developments in clostridial acetone/butanol/isopropanol fermentationAppl. Microbiol. Biotechnol. 49:639-648, 1998.

Eichenbaum, et al., Use of the Lactococcal nisA Promoter to Regulate Gene Expression in Gram-Positive Bacteria: Comparison of Induction Level and Promoter Strength, Appl. Environ. Microbiol. 64:2763-2769, 1998.

Fleming, et al., Extracellular Enzyme Synthesis in a Sporulation-Deficient Strain of Bacillus licheniformis, Appl. Environ. Microbiol. 61:3775-3780, 1995.

Flint, et al., The Role and Properties of the Iron-Sulfur Cluster in *Escherichia coli* Dihydroxy-acid Dehydratase, J. Biol. Chem. 268:14732-14742, 1993.

Ford, et al., Characterization of Yprlp from *Saccharomyces cerevisiae* as a 2-methylbutyraldehyde reductase, Yeast 19:1087-1096, 2002.

Fujimoto, et al., pAM401-Based Shuttle Vectors That Enable Overexpression of Promoterless Genes and One-Step Purification of Tag Fusion Proteins Directly from Enterococcus faecalis, Appl. Environ. Microbiol. 67:1262-1267, 2001.

Gollop, et al., Physiological Implications of the Substrate Specificities of Acetohydroxy Acid Synthases from Varied Organisms, J. Bacteriol. 172:3444-3449, 1990.

Groot, et al., Technologies for Butanol Recovery Integrated with Fermentations, Process. Biochem. 27:61-75, 1992.

Guex, et al., Swiss-Model and the Swiss-PdbViewer: An Environment for Comparative Protein Modeling, Electrophoresis 18:2714-2723, 1997.

Hermann, et al., Isolation and Characterization of Butanol-Resistant Mutants of Clostridium acetobutylicum, Appl. Environ. Microbiol. 50:1238-1243, 1985.

Holtzclaw, et al., Degradative Acetolactate Synthase of Bacillus subtilis: Purification and Properties, J. Bacteriol. 121:917-922, 1975.

Jones, et al., Improved Methods for Building Protein Models in Electron Density Maps and the Location of Errors in these Models, Acta Crystallogr. A 47:110-119, 1991.

Kabelitz, et al., Effect of aliphatic alcohols on growth and degree of saturation of membrane lipids in Acinetobacter calcoaceticus, FEMS Microbiol. Lett. 220: 223-227, 2003.

Datsenko, et al., One-step inactivation of chromosomal genes in *Escherichia coli* K-12 using PCR products, Proc. Natl. Acad. Sci. USA 97:6640-6645, 2000.

Kleerebezem, et al., Controlled Gene Expression Systems for Lactic Acid Bacteria: Transferable Nisin-Inducible Expression Cassettes for *Lactococcus, Leuconostoc,* and *Lactobacillus* spp., Appl. Environ. Microbiol. 63:4581-4584, 1997.

Kostichka, et al., A small cryptic plasmid from Rhodococcus erythropolis: characterization and utility for gene expressionAppl. Microbiol. Biotechnol. 62:61-68, 2003.

Krogh, et al., Hidden Markov Models in Computational Biology, J. Mol. Biol. 235:1501-1531, 1994.

Larroy, et al., Characterization of the *Saccharomyces cerevisiae* YMR318C (ADH6) gene product as a broad specificity NADPH-dependent alchohol dehydrogenase: relevance in aldehyde reduction, Biochem. J. 361:163-172, 2002.

Maguin, et al., New Termosensitive Plasmid for Gram-Positive Bacteria, J. Bacteriol. 174:5633-5638, 1992.

Marinus, et al., Regulation of Isoleucine-Valine Biosynthesis in Pseudomonas aeruginosa, Genetics 63:547-56, 1969.

Nagarajan, et al., Modular Expression and Secretion Vectors for Bacillus subtilis, Gene 114:121-126, 1992.

Nakashima et al., Isolation and Characterization of a Rolling-Circle-Type Plasmid from Rhodococcus erythropolis and Application of the Plasmid to Multiple-Recombinant-Protein Expression, Appl. Environ. Microbiol. 70:5557-5568, 2004.

Nallaapareddy, et al., Construction of Improved Temperature-Sensitive and Mobilizable Vectors and Their Use for Constructing Mutations in the Adhesin-Encoding acm Gene of Poorly Transformable Clinical Enterococcus faecium Strains, Appl. Environ. Microbiol. 72:334-345, 2006.

O'Sullivan, et al., High- and low-copy-number Lactococcus shuttle cloning vectors with features for clone screening, Gene 137:227-231, 1993.

Payne, et al., Use of Alkaline Phosphatase Fusions to Study Protein Secretion in Bacillus subtilis, J. Bacteriol. 173:2278-2282, 1991.

Renault, et al., Plasmid Vectors for Gram-positive Bacteria Switching from High to Low Copy Number, Gene 183:175-182, 1996.

Scott, et al., Sequences of versatile broad-host-range vectors of the RK2 family, Plasmid 50:74-79, 2003.

Smit, et al., Identification, Cloning, and Characterization of a Lactococcus lactis Branched-Chain alpha-Keto Acid Decarboxylase Involved in Flavor Formation, Appl. Environ. Microbiol. 71:303-311, 2005.

Sulter, et al., Proliferation and metabolic significance of peroxisomes in Candida boidinii during drowth on D-alanine or oleic acid as the sole carbon source, Arch. Microbiol. 153:485 489, 1990.

Sulzenbacher, et al., Crystal Structure of *E. coli* Alcohol Dehydrogenase YqhD: Evidence of a Covalently Modified NADP Coenzyme, J. Mol. Biol. 342:489-502, 2004.

Tabor, et al., A bacteriophage T7 RNA polymerase/promoter system for controlled exclusive expression of specific genes, Proc. Acad. Sci. USA 82:1074, 1985.

Taghavi, et al., Electroporation of Alcaligenes eutrophus with (Mega) Plasmids and Genomic DNA Fragments, Appl. Environ. Microbiol. 60:3585-3591, 1994.

Tanimoto, et al., Analysis of the Conjugal Transfer System of the Pheromone-Independent Highly Transferable Enterococcus Plasmid pMG1: Identification of a tra Gene (traA) Up-Regulated during Conjugation, J. Bacteriol. 184:5800-5804, 2002.

Tao, et al., Construction of highly efficient *E. coli* expression systems containing low oxygen induced promoter and partition region, Appl. Microbiol. Biotechnol. 68:346-354, 2005.

Thompson, et al., Clustal W: improving the sensitivity of progressive multiple sequence alignment through sequence weighting, position-specific gap penalties and weight matrix choice, Nuc. Acid Res. 22:4673-4680, 1994.

Tomas, et al., Transcriptional Analysis of Butanol Stress and Tolerance in Clostridium acetobutylicum, J. Bacteriol. 186:2006-2018, 2004.

Pearson, Comput. Methods Genome Res., [Proc. Int. Symp.] (1994), Meeting Date 1992, 111-20. Editor(s): Suhai, Sandor. Plenum: New York, NY.

van Kranenburg, et al., Functional Analysis of Three Plasmids from Lactobacillus plantarum, Appl. Environ. Microbiol. 71:1223-1230, 2005.

Walker, et al. Isothermal in vitro amplification of DNA by restriction enzyme/DNA polymerase systemProc. Natl. Acad. Sci. U.S.A. 89:392-396, 1992.

Wyckoff, et al., Characterization and Sequence Analysis of a Stable Cryptic Plasmid from Enterococcus faecium 226 and Development of a Stable Cloning Vector, Appl. Environ. Microbiol. 62:1481-1486, 1996.

Dumas, et al., Purification and characterization of a fusion protein of plant acetohydroxy acid synthase and acetohydroxy acid isomeroreductase, FEBS Lett. 408:156-160, 1997.

Bellion et al., Microb. Growth C1 Compd., [Int. Symp.], 7th (1993), 415 32. (eds): Murrell, J. Collin; Kelly, Don P. Publisher: Intercept, Andover, UK.

Dumas, et al., Isolation and kinetic properties of acetohydroxy acid isomeroreductase from spinach (*Spinacia oleracea*) chloroplasts overexpressed in *Escherichia coli*, Biochem. J. 288:865-874, 1992.

Yuan, et al. Regulation of groE Expression In Bacillus subtills: the Involvment of cr -Like Promoter and the Roles of the Inverted Repeat Sequence (CIRCE), J. Bacterial. 177:5427-5433, 1995.

(56) References Cited

OTHER PUBLICATIONS

Yansura, et al., Use of the *Escherichia coli* lac repressor and operator to control gene expression in Bacillus subtilis, Proc. Natl. Acad. Sci. USA, vol. 81:439-443, 1984.
Rud, et al., A synthetic promoter library for constitutive gene expression in lactobacillus plantarum, Microbiol. 152:1011-1019, 2006.
Johnson, et al., DNA sequences at the ends of transposon Tn5 required for transposition, Nature 304:280-282, 1983.
Rothstein, Targeting, disruption, replacement, and allele rescue: integrative DNA transformation in yeast, Meth. Enzymol. 194:281-301, 1991.
Horton, et al., Engineering hybrid genes without the use of restriction enzymes: gene splicing by overlap extension, Gene 77:61-68, 1989.
Kaneko, et al., Complete Genome Sequence of the Filamentous Nitrogen-fixing *Cyanobacterium anabaena* sp. strain PCC 7120, DNA Res. 8:205-213, 227-253, 2001.
Higgins et al., Fast and sensitive multiple sequence alignments on a microcomputer, CABIOS Communications 5:151-153, 1989.
Higgins, et al., CLUSTAL V: improved software for multiple sequence alignment, CABIOS 8:189-191, 1992.
Eppink, et al., Switch of Coenzyme Specificity of p-Hydroxybenzoate Hydroxylase, J. Mol. Biol. 292:87-96, 1999.
Nakanishi, et al., Switch of Coenzyme Specificity of Mouse Lung Carbonyl Reductase by Substitution of Threonine 38 with Aspartic Acid, J. Biol. Chem. 272:2218-2222, 1997.
Kamerbeek, et al., Identifying Determinants of NADPH Specificity in Baeyer-Villiger Monooxygenases, Eur. J. Biochem. 271:2107-2116, 2004.
Nishiyama, et al., Alteration of Coenzyme Specificity of Malate Dehydrogenase from Thermus flavus by Site-directed Mutagenesis, J. Biol. Chem. 268:4656-4660, 1993.
Martinez-Julvez, et al., Towards a New Interaction Enzyme: Coenzyme, Biophys. Chem. 115:219-224, 2005.
Horinouchi, et al., Nucleotide sequence and functional map of pE194, a plasmid that specifies inducible resistance to macrolide, lincosamide, and streptogramin type B antibiotics, J. Bacteriol. 150:804-814, 1982.
Godon. et al., Branched-chain amino acid biosynthesis genes in *Lactococcus lactic* subsp. lactis, J. Bacteriol. 174:6580-6589, 1992.
Ferain, et al., Lactobacillus plantarum IdhL gene: overexpression and deletion, J. Bacteriol. 176:596-601, 1994.
Carugo, et al., NADP-Dependent Enzymes I: Conserved Stereochemistry of Cofactor Binding, Proteins: Structure, Function, and Genetics 28:10-28, 1997.
Dumas, et al., Enzymology. Structure, and Dynamics of Acetohydroxy Acid Isomeroreductase, Acc. Chem. Res. 34:399-408, 2001.
Elmore, et al., Modification of the Nucleotide Cofactor-binding Site of Cytochrome P-450 Reductase to Enhance Turnover with NADH in vivo, J. Biol. Chem. 277:48960-48964, 2002.
Fisher, et al., The X-ray Structure of Brassica napus beta-keto acyl carrier protein reductase and its implication for substrate binding and catalysis, Structure 8:339-347, 2000.
Khoury, et al., Computational design of Candida boidinii xylose reductase for altered cofactor specificity, Protein Sci. 18:2125-2136, 2009.
Kuzuyama, et al., Characterization of 1-deoxy-D-xylulose 5-Phosphate Reductoisomerase, an Enzyme Involved in Isopentenyl Diphosphate Biosynthesis, and Identification of Its Catalytic Amino Acid Residues, J. Biol. Chem. 275:19928-19932, 2000.
Medina, et al., Probing the Determinants of Coenzyme Specificity in Ferredoxin-NADP+ Reductase by Site-directed Mutagenesis, J. Biol. Chem. 276:11902-11912, 2001.
Wierenga, et al., Prediction of the Occurence of the SDP-binding Beta-alpha-beta Fold in Proteins, Using an Amino Acid Sequence Fingerprint, J. Mol. Biol. 187:101-107, 1986.
Brinkmann-Chen, et al., General approach to reversing ketol-acid reductoisomerase cofactor dependence from NADPH to NADH, Proc. Natl. Acad. Sci. 110:10946-10951, 2013.
Rossmann, et al., Chemical and biological evolution of nucleotide-binding protein, Nature 250:194-199, 1974.
Curien, et al., Nucleotide sequence and characterization of a cDNA encoding the acetohydroxy acid isomeroreductase from Arabidopsis thaliana, Plant Molecular Biology 21:717-722, 1993.
Dumas, et al., Purification and characterization of acetohydroxyacid reductoisomerase from spinach chloroplasts, Biochem. J. 262:971-976, 1989.
Chang, et al., Construction and Characterization of Amplifiable Multicopy DNA Cloning Vehicles Derived from the P15A Cryptic Minplasmid, J. Bacteriol. 134:1141-1156, 1978.
Feeney, et al., a single amino acid substitution in lactate dehydrogenase improves the catalytic efficiency with an alternative coenzyme, Biochem. Biophys. Res. Commun. 166:667-672, 1990.
Inui, et al., Identification and sequence determination of the acetohydroxy acid isomeroreductase gene from Brevibacterium flavum MJ233, DNA Seq. 4:95-103, 1993 (Abstract).
Lauvergeat, et al., Site-directed mutagenesis of a serine residue in cinnamyl alcohol dehydrogenase, a plant NADPH-dependent dehydrogenase, affects the specificity for the coenzyme, Biochemistry 34:12426-12434, 1995.
Levskaya, et al., Synthetic biology: engineering *Escherichia coli* to see light, Nature 438:441-442, 2005.
Shiraishi, et al., Engineering of pyridine nucleotide specificity of nitrate reductase: mutagenesis of recombinant cytochrome b reductase fragment of Neurospora crassa NADPH:Nitrate reductase, Archives of Biochemistry and Biophysics 358:104-115, 1998.
Tyagi, et al., Probing the mechanism of the bifunctional enzyme ketol-acid reducoisomerase by site-directed mutagenesis of the active site, FEBS Journal 272:593-602, 2005.
Zhang, et al., Change of nucleotide specificity and enhancement of catalytic efficiency in single point mutants of Vibrio harveyi aldehyde dehydrogenase, Biochemistry 38:11440-11447, 1999.
Altschul, et al., Basic Local Alignment Search Tool, J. Mol. Biol. 215:403-410, 1990.
Davison, et al. Continuous Direct Solvent Extration of Butanol in a Fermenting Fluidized-Bed Bioreactor with Immobilized Clostridium acetobutylicum. Appl. Biochem. Biotech. 39/40:415-426, 1993.
EBI Accession No. UniProt: Q8ZAC2, Entry Date Jun. 6, 2003.
EBI Accession No. UniProt: Q0AV19, Entry Date Jan. 15, 2008.
EBI Accession No. UniProt: Q02138, Entry Date Jul. 1, 1993.
EBI Accession No. UniProt: Q01292, Entry Date Apr. 1, 1993.
EBI Accession No. UniProt: P06168, Entry Date Jan. 1, 1988.
EBI Accession No. UniProt: P05793, Entry Date Nov. 1, 1988.
EBI Accession No. UniProt: B1ZV88, Entry Date Jun. 6, 2003.
She, et al., Q97YJ9—UNIPROTKB/Swiss-Prot. Database, Oct. 31, 2006.
Suerbaum, et al., UniProtKB Database, Accession Q7VGW6, 2003.
Kaneko, et al., Q8YUM—UniProt Database, Mar. 23, 2010.
GenBank No. NC_009135.1, Methanococcus maripaludis C5, complete genome, Apr. 30, 2009.
GenBank No. NC_005791.1, Methanococcus maripaludis S2, complete genome, Apr. 25, 2009.
GenBank No. NZ_AAWX01000002.1, Copeland, et al., Feb. 7, 2007; pp. 1-3.
GenBank No. NC_001144.4, *Saccharomyces cerevisiae* chromosome XII, complete sequence, Jun. 16, 2008.
GenBank No. NC_002754.1, Sulfolobus solfataricus P2, complete genome, Apr. 26, 2009.
GenBank No. NC_003364.1, Pyrobaculum aerophilum str. IM2, complete genome, Apr. 24, 2009.
GenBank No. AAA25079, acetolactate synthase [Klebsiella pneumoniae], Aug. 5, 1994.
GenBank No. AAA25161, alpha-acetolactate synthase, Apr. 21, 1994.
GenBank No. AAA65614, keto acid dehydrogenase E1-alpha subunit [Pseudomonas putida] Feb. 27, 2002.
GenBank No. AAA65615, 39 kDa keto acid dehydrogenase El-beta subunit [Pseudomonas putida], Feb. 27, 2002.
GenBank No. AAA65617, transacylase E2 [Pseudomonas putida], Feb. 27, 2002.
GenBank No. AAA65618, lipoamide dehydrogenase [Pseudomonas putida], Feb. 27, 2002.

(56) References Cited

OTHER PUBLICATIONS

GenBank No. AAS49166, branched-chain alpha-ketoacid decarboxylase [Lactococcus lactis], Dec. 27, 2004.
GenBank No. AJ746364, *Lactococcus lactis* subsp. lactis kivd gene for alpha-ketoisovalerate decarboxylase, strain IFPL730, Apr. 15, 2005.
GenBank No. AY548760, Lactococcus lactis branched-chain alpha-ketoacid decarboxylase (kdcA) gene, complete cds, Dec. 27, 2004.
GenBank No. BX950229, Methanococcus maripaludis strain S2, complete sequence, May 8, 2008.
GenBank No. CAB14105, dihydroxy-acid dehydratase [*Bacillus subtilis* subsp. *subtilis* str, Oct. 1, 2009.
GenBank No. CAB14334, branched-chain alpha-keto acid dehydrogenase E2 subunit (lipoamide acyltransferase) [*Bacillus subtilis* subsp. *subtilis* str. 1681 Oct. 1, 2009.
GenBank No. CAB14335, branched-chain alpha-keto acid dehydrogenase E1 subunit [*Bacillus subtilis*subsp. *subtilis* str. 168], Oct. 1, 2009.
GenBank No. CAB14336, branched-chain alpha-keto acid dehydrogenase El subunit [*Bacillus subtilis* subsp. *subtilis* str. 168], Oct. 1, 2009.
GenBank No. CAB14337, branched-chain alpha-keto acid dehydrogenase E3 subunit (dihydrolipoamide dehydrogenase) [*Bacillus subtilis* subsp. *subtilis* str. 168], Oct. 1, 2009.
GenBank No. CAB15618, alpha-acetolactate synthase [*Bacillus subtilis* subsp. *subtilis* str. 168], Oct. 1, 2009.
GenBank No. CAF29874, Dihydroxy-acid dehydratase [Methanococcus maripaludis S2], May 8, 2008.
GenBank No. CAG34226, alpha-ketoisovalerate decarboxylase [*Lactococcus lactis* subsp. *lactis*], Apr. 15, 2005.
GenBank No. L16975, Lactococcus lactis alpha-acetolactate synthase (als) gene, complete cds, Apr. 21, 1994.
GenBank No. M57613, Pseudomonas putida branched-chain keto acid dehydrogenase operon (bkdA1, bkdA1 and bkdA2), transacylase E2 (bkdB), bkdR and lipoamide dehydrogenase (IpdV) genes, complete cds, Feb. 27, 2002.
GenBank No. M73842, Klebsiella pneumoniae acetolactate synthase (iluk) gene, complete cds, Aug. 5, 1994.
GenBank No. NC_001142, Nosema ceranae BRL01 Nc001142, whole genome shotgun sequence, Jun. 9, 2009.
GenBank No. NC_003030, Clostridium acetobutylicum ATCC 824, complete genome, Oct. 22, 2009.
GenBank No. NC_001136, *Saccharomyces cerevisiae* chromosome IV, complete sequence, Dec. 9, 2009.
GenBank No. NC_001145, *Saccharomyces cerevisiae* chromosome XIII, complete sequence, Dec. 9, 2009.
GenBank No. NC_001988, Clostridium acetobutylicum ATCC 824 plasmid pSOL1, complete sequence, Apr. 26, 2009.
GenBank No. NC_003197, *Salmonella typhimurium* LT2, complete genome, Mar. 30, 2010.
GenBank No. NP_012550, Dihydroxyacid dehydratase, catalyzes third step in the common pathway leading to biosynthesis of branchedchain amino acids; llv3p [*Saccharomyces cerevisiae*], Nov. 5, 2009.
GenBank No. NP_010656, Jacq, et al., downloaded Apr. 15, 2010, pp. 1-3.
GenBank No. NP_014051, Adh6p [*Saccharomyces cerevisiae*], Dec. 9, 2009.
GenBank No. NP_149189, pyruvate decarboxylase [Clostridium acetobutylicum ATCC 824], Apr. 26, 2009.
GenBank No. NP_349892, NADH-dependent butanol dehydrogenase A (BDH I) [Clostridium acetobutylicum ATCC 824], Apr. 14, 2010.
GenBank No. NP_417484, alcohol dehydrogenase, NAD(P)-dependent [*Escherichia coli* str. K-12 substr. MG1655], Apr. 9, 2010.
GenBank No. NP_461346, indolepyruvate decarboxylase [*Salmonella typhimurium* LT2], Apr. 30, 2009.
GenBank No. YP_026248, dihydroxyacid dehydratase [*Escherichia coli* str. K-12 substr. MG1655], Jul. 30, 2009.
GenBank No. Z99115, Bacillus subtilis complete genome (section 12 of 21): from 2207806 to 2409180, Nov. 15, 2007.
GenBank No. AL009126, *Bacillus subtilis* subsp. subtilis str. 168 complete genome, Oct. 1, 2009.
GenBank No. Z99122, Bacillus subtilis complete genome (section 19 of 21): from 3608981 to 3809670, Apr. 18, 2005.
GenBank No. ZP01224863.1, ketol-acid reductoisomerase [marine gamma proteobacterium HTCC2207], Mar. 24, 2006.
GenBank No. NC_003295.1, Ralstonia solanacearum GMI1000, complete genome, May 1, 2009.
GenBank Accession No. ZP_07930881, ketol-acid reductoisomerase [*Anaerostipes* sp. 3_2_56FAA], Nov. 27, 2012.
GenBank Accession No. YP_162876, ketol-acid reductoisomerase [*Zymomonas mobilis* subsp. *mobilis* ZM4 = ATCC 31821], Jun. 10, 2013.
GenBank No. ZP_01313517.1, ketol-acid reductoisomerase [Desulfuromonas acetoxidans DSM 684], May 15, 2006.
GenBank No. O82043, Ketol-acid reductoisomerase, chloroplastic, Jun. 16, 2009.
GenBank No. NP_977840.1, ketol-acid reductoisomerase [Bacillus cereus ATCC 10987], May 1, 2009.
GenBank No. NP_978252.1, ketol-acid reductoisomerase [Bacillus cereus ATCC 10987], May 1, 2009.
GenBank No. P05793, Daniels, et al., Jun. 16, 2009; pp. 1-9.
Entrez GenBank Accession No. UNIPROT: Q6F821, Barbe, et al., Oct. 2004; pp. 1-2.
GenBank Accession No. B9CVH4, viewed Feb. 8, 2011.
GenBank EDR97797.1 Feb. 12, 2008. 1 page.
Kumanovics, et al. Identification of FRA 1 and FRA2 as genes involved in regulating the yeast iron regulon in response to decreased mitochondrial iron-sulfur cluster synthesis. J. Biol. Chem. 283:10276-10286, 2008.
Methods in Yeast Genetics, 2005, Cold Spring Harbor Laboratory Press, Cold Spring Harbor, NY, pp. 201-202.
U.S. Appl. No. 14/571,817, filed Dec. 16, 2014 (Butamax).
U.S. Appl. No. 14/585,261, filed Dec. 30, 2014 (Butamax).

* cited by examiner

FERMENTIVE PRODUCTION OF ISOBUTANOL USING HIGHLY ACTIVE KETOL-ACID REDUCTOISOMERASE ENZYMES

CROSS-REFERENCE TO RELATED APPLICATIONS

This application is a Continuation Application of U.S. application Ser. No. 12/103,844, filed Apr. 16, 2008, now U.S. Pat. No. 7,910,342, which claims priority benefit of U.S. Provisional Application No. 60/912,491, filed Apr. 18, 2007.

FIELD OF THE INVENTION

The invention relates to the field of industrial microbiology and production of alcohols. More specifically, isobutanol is produced via industrial fermentation of a recombinant microorganism using special ketol-acid reductoisomerase (KARI) enzymes with high turnover numbers. This invention also relates to methods for discovering highly active KARI enzymes from natural microorganisms.

BACKGROUND OF THE INVENTION

Butanol is an important industrial chemical, useful as a fuel additive, as a feedstock chemical in the plastics industry, and as a foodgrade extractant in the food and flavor industry. Each year 10 to 12 billion pounds of butanol are produced by petrochemical means and the need for this commodity chemical will likely increase.

Methods for the chemical synthesis of isobutanol are known, such as oxo synthesis, catalytic hydrogenation of carbon monoxide (*Ullmann's Encyclopedia of Industrial Chemistry*, 6$^{th}$ edition, 2003, Wiley-VCHVerlag GmbH and Co., Weinheim, Germany, Vol. 5, pp. 716-719) and Guerbet condensation of methanol with n-propanol (Carlini et al., *J. Molec. Catal. A:Chem.* 220, 215-220, 2004). These processes use starting materials derived from petrochemicals and are generally expensive and are not environmentally friendly. The production of isobutanol from plant-derived raw materials would minimize green house gas emissions and would represent an advance in the art.

Isobutanol is produced biologically as a by-product of yeast fermentation. It is a component of "fusel oil" that forms as a result of incomplete metabolism of amino acids by this group of fungi. Isobutanol is specifically produced from catabolism of L-valine. After the amine group of L-valine is harvested as a nitrogen source, the resulting α-keto acid is decarboxylated and reduced to isobutanol by enzymes of the so-called Ehrlich pathway (Dickinson et al., *J. Biol. Chem.* 273, 25752-25756, 1998). Yields of fusel oil and/or its components achieved during beverage fermentation are typically low. For example, the concentration of isobutanol produced in beer fermentation is reported to be less than 16 parts per million (Garcia et al., *Process Biochemistry* 29, 303-309, 1994). Addition of exogenous L-valine to the fermentation increases the yield of isobutanol, as described by Dickinson et al., supra, wherein it is reported that a yield of isobutanol of 3 g/L is obtained by providing L-valine at a concentration of 20 g/L in the fermentation. In addition, production of n-propanol, isobutanol and isoamylalcohol has been shown by calcium alginate immobilized cells of *Zymomonas mobilis*. A 10% glucose-containing medium supplemented with either L-Leu, L-Ile, L-Val, alpha-ketoisocaproic acid (alpha-KCA), alpha-ketobutyric acid (alpha-KBA) or alpha-ketoisovaleric acid (alpha-KVA) was used (Oaxaca, et al., Acta Biotechnol.; 11, 523-532, 1991). Alpha-KCA increased isobutanol levels. The amino acids also gave corresponding alcohols, but to a lesser degree than the keto acids. An increase in the yield of C3-C5 alcohols from carbohydrates was shown when amino acids leucine, isoleucine, and/or valine were added to the growth medium as the nitrogen source (WO 2005040392).

While methods described above indicate the potential of isobutanol production via biological means these methods are cost prohibitive for industrial scale isobutanol production. The biosynthesis of isobutanol directly from sugars would be economically viable and would represent an advance in the art. However, this production is severely hampered by the slow ketol-acid reductoisomerase (KARI) enzyme that catalyzes the second step in the iso-butanol pathway that converts acetolactate to dihydroxy-isovalerate. Because this enzyme is already expressed at high levels (S. Epelbaum et al. *J. Bacteriol.*, 180, 4056-4067, 1998), there is a need to increase the activity of KARI, without increasing the amount of protein, i.e. increase the enzyme specific activity.

Applicants have solved the stated problem through the discovery of a KARI enzyme having a high specific activity which can be used to enhance the biological production of isobutanol.

SUMMARY OF THE INVENTION

The invention relates to recombinant organisms expressing highly active KARI enzymes. The engineered microorganism will have high levels of the short form of KARI enzyme which possesses significantly higher specific activity (6-8 times of the KARI enzyme in *E. coli*) and may be used for the commercial production of isobutanol. Accordingly, in one embodiment the invention provides a method for conversion of acetolactate to dihydroxy-isovalerate comprising:
    a) providing a microbial host cell comprising genetic construct encoding a polypeptide having ketol-acid reductoisomerase specific activity greater than that of the specific activity of an *E. coli* ketol-acid reductoisomerase; and
    b) contacting the host cell of (a) with acetolactate wherein 2,3-dihydroxy-isovalerate is produced.

In a preferred embodiment the genetic construct encodes a polypeptide having ketol-acid reductoisomerase specific activity of greater than 1.1 μmoles/min/mg based on purified protein as measured by the NADPH consumption assay, run under the following conditions:
    a) pH of about 7.5;
    b) a temperature of about 22.5° C.; and
    c) greater than about 10 mM potassium.

In another embodiment the invention provides a method for the production of isobutanol comprising:
    a) providing a recombinant microbial host cell comprising the following genetic constructs:
        1) at least one genetic construct encoding an acetolactate synthase enzyme of the conversion of pyruvate to acetolactate (pathway step a);
        2) at least one genetic construct encoding a ketol-acid reductoisomerase enzyme specific activity of greater than 1.1 μmoles/min/mg based on purified protein as measured by the NADPH consumption assay, run under the following conditions:
            i) pH of about 7.5;
            ii) a temperature of about 22.5° C.; and
            iii) greater than about 10 mM potassium for the conversion of (S)-acetolactate to 2,3-dihydroxyisovalerate, (pathway step b);

3) at least one genetic construct encoding an acetohydroxy acid dehydratase for the conversion of 2,3-dihydroxyisovalerate to α-ketoisovalerate, (pathway step c);
4) at least one genetic construct encoding a branched-chain keto acid decarboxylase, of the conversion of α-ketoisovalerate to isobutyraldehyde, (pathway step d);
5) at least one genetic construct encoding a branched-chain alcohol dehydrogenase for the conversion of isobutyraldehyde to isobutanol (pathway step e); and b) growing the host cell of (a) under conditions where iso-butanol is produced.

In another embodiment the invention provides a recombinant host cell comprising a ketol-acid reductoisomerase enzyme having a specific activity greater than the specific activity of an *E. coli* ketol-acid reductoisomerase.

In another embodiment the invention provides a method for the identification and isolation of a genetic construct encoding a ketol-acid reductoisomerase enzyme having a specific activity of greater than 1.1 μmoles/min/mg based on purified protein as measured by the NADPH consumption assay, run under the following conditions:
  i) pH of about 7.5;
  ii) a temperature of about 22.5° C.; and
  iii) greater than about 10 mM potassium;
comprising the steps of:
  a) identifying bacterial species having a doubling time shorter than that of *E. coli* when grown in M9 minimal medium;
  b) screening the bacterial species of (a) for ketol-acid reductoisomerase activity to identify active bacterial species;
  c) probing the genomic DNA of the active bacterial species of (b) with nucleic acid sequences having homology to genetic constructs known to encode a ketol-acid reductoisomerase to identify and isolate genetic constructs encoding a ketol-acid reductoisomerase from said active bacterial species; and
  d) amplifying and expressing the genetic constructs encoding a ketol-acid reductoisomerase from said active bacterial species; and
  e) screening the expressed genetic constructs of step (d) for those having a specific activity of greater than 1.1 μmoles/min/mg based on purified protein as measured by the NADPH consumption assay, run under the following conditions:
    i) pH of about 7.5;
    ii) a temperature of about 22.5° C.; and
    iii) greater than about 10 mM potassium.

BRIEF DESCRIPTION OF THE FIGURES AND SEQUENCES OF THE INVENTION

The invention can be more fully understood from the following detailed description, the FIGURE, and the accompanying sequence descriptions, which form part of this application.

Figure 1B:
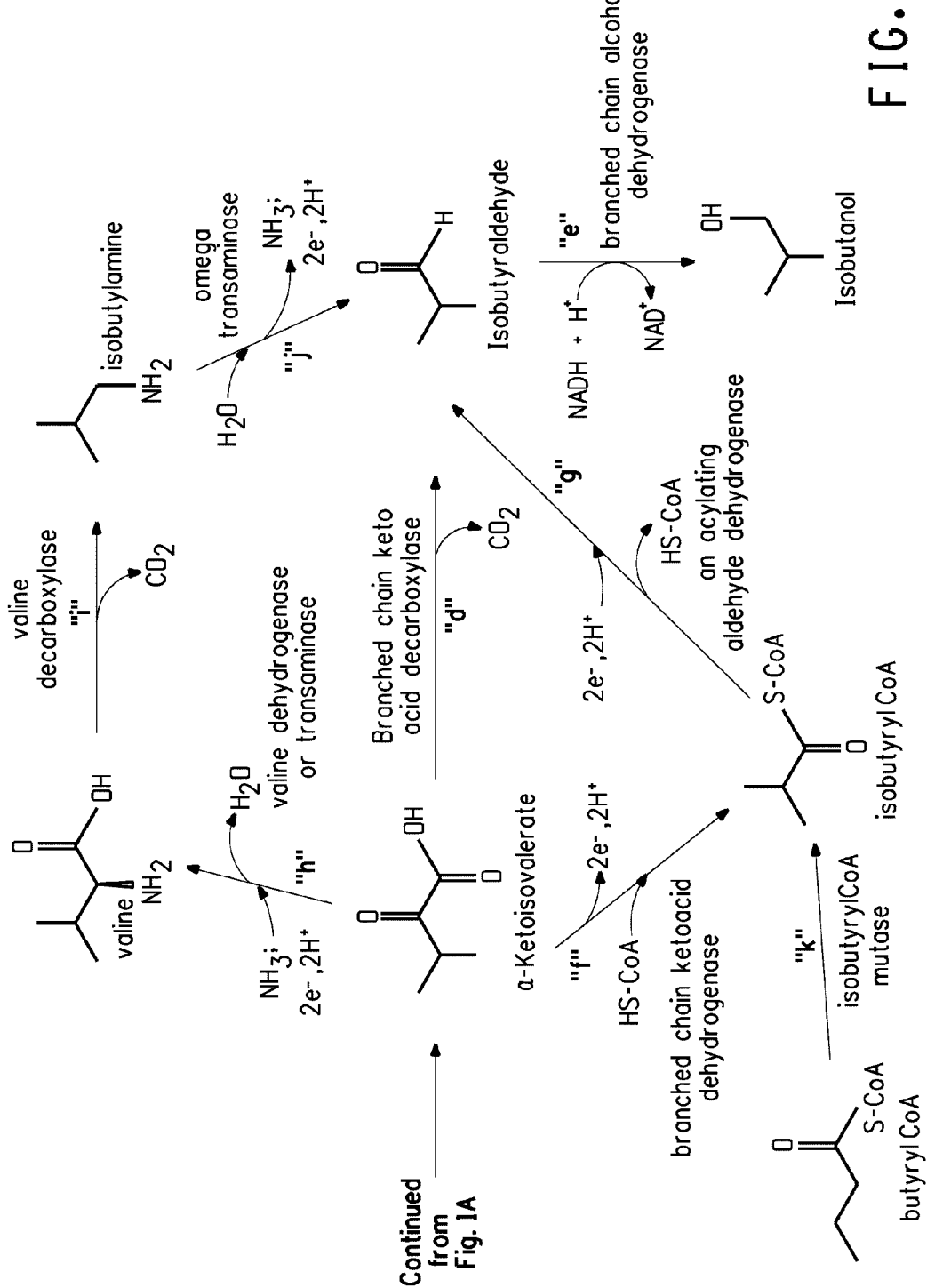

FIGS. 1A and 1B show four different isobutanol biosynthetic pathways. The steps labeled "a", "b", "c", "d", "e", "f", "g", "h", "i", "j" and "k" represent the substrate to product conversions described below.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

Summary of Gene and Protein SEQ ID Numbers of the Preferred Isobutanol Pathway

| Description | SEQ ID NO: Nucleic acid | SEQ ID NO: Peptide |
|---|---|---|
| *Klebsiella pneumoniae* budB (acetolactate synthase) | 1 | 2 |
| *E. coli* ilvC (acetohydroxy acid reductoisomerase) | 3 | 4 |
| *E. coli* ilvD (acetohydroxy acid dehydratase) | 5 | 6 |
| *Lactococcus lactis* kivD (branched-chain α-keto acid decarboxylase), codon optimized | 7 | 8 |
| *E. coli* yqhD (branched-chain alcohol dehydrogenase) | 9 | 10 |

SEQ ID NOs: 11-22 are the nucleotide sequences of oligonucleotide primers used to generate the constructs in Example 1.

SEQ ID NOs: 23-30 are the nucleotide sequences of oligonucleotide primers used to generate the constructs in Example 2.

SEQ ID Nos. 11 and 12 are the DNA sequences of the primers used in Example 1 for PCR amplification of ilvC gene SEQ ID No. 13 is the forward DNA sequence for the primer used to clone the KARI gene in the pBAD vector in *E. coli*

SEQ ID No. 14 is the reverse DNA sequence for the primer used to clone the KARI gene in the pBAD vector in *E. coli*

SEQ ID No. 15 is the forward DNA sequence for ilvC-trc-SacI-F used to amplify the KARI gene SEQ ID No. 16 is the reverse DNA sequence for ilvC-trc-HindIII-R used to amplify the KARI gene SEQ ID Nos. 17 to 22 are the nucleotide sequences of oligonucleotide primers used to confirm the presence of *E. coli* ilvC insert by SacI digestion and DNA sequencing
  SEQ ID No. 17—ilvC-trc-F3
  SEQ ID No. 18—ilvC-trc-F5
  SEQ ID No. 19—ilvC-trc-R2
  SEQ ID No. 20—ilvC-trc-R4
  SEQ ID No. 21—pBAD-eF1
  SEQ ID No. 22—PALPK-R1

SEQ ID Nos. 23 to 26 are the nucleotide sequences of oligonucleotide primers used in the forward and reverse directions to amplify the ilvC genes from the genomic DNA of *Pseudomonas aeruginosa* (PAO1) and *Pseudomonas fluorescens* (PF5) by PCR.
  SEQ ID #23—PAO1-C-F1
  SEQ ID No. 24—PAO1-C-R1
  SEQ ID No. 25—PF5-C-F1
  SEQ ID No. 26—PF5-C-R1

SEQ ID No. 21, 22, 27 and 28 are the nucleotide sequences of oligonucleotide primers used to validate the DNA sequences of the positive clones containing the ilvC genes of *Pseudomonas*.
  SEQ ID No. 27—PF5-S-F2
  SEQ ID No. 28—PF5-S-R2

The following SEQ ID NO's correspond to the DNA sequences of the KARI genes used in this invention:

SEQ ID No. 29—*E. coli* K12-ilvC
SEQ ID No. 30—codon optimized KARI from *Vibrio* for *E. coli* expression
SEQ ID No. 31—*Pseudomonas aeruginosa*—PAO1—ilvC
SEQ ID No. 32—*Pseudomonas fluorescens*—PF5—ilvC
The following SEQ ID NO's are the amino acid sequences corresponding SEQ ID NO's 29-32 respectively:
SEQ ID No. 33—*E. coli* K12—ilvC—[KARI from *E. coli* K12]
SEQ ID No. 34—KARI from *Vibrio cholerae*
SEQ ID No. 35—PAO1-ilvC (1 as-338 aa)
SEQ ID No. 36—PF5-ilvC (1 as-338aa)
SEQ ID No. 37 is the forward primer PAL-F1
SEQ ID No. 38 is the Reverse primer (PAL-R1)
SEQ ID No. 39 is the Forward primer (PAL-EcoR1-F1)
SEQ ID No. 40 is the Reverse primer (PAL-EcoR1-R1)

DETAILED DESCRIPTION OF THE INVENTION

The present invention relates to a method for conversion of acetolactate to 2,3-dihydroxy-isovalerate using microbial host cells containing a very active KARI enzyme. The 2,3-dihydroxy-isovalerate thus formed is further converted via steps shown in FIG. 1 to isobutanol. The invention also discloses methods to find faster KARI enzymes in their natural host microorganisms and molecular evolution of such enzymes for the purpose of further improving their catalytic activity.

The present invention meets a number of commercial and industrial needs. Butanol is an important industrial commodity chemical with a variety of applications, where its potential as a fuel or fuel additive is particularly significant. Although only a four-carbon alcohol, butanol has an energy content similar to that of gasoline and can be blended with any fossil fuel. Butanol is favored as a fuel or fuel additive as it yields only $CO_2$ and little or no $SO_X$ or $NO_X$ when burned in the standard internal combustion engine. Additionally butanol is less corrosive than ethanol, the most preferred fuel additive to date.

In addition to its utility as a biofuel or fuel additive, butanol has the potential of impacting hydrogen distribution problems in the emerging fuel cell industry. Fuel cells today are plagued by safety concerns associated with hydrogen transport and distribution. Butanol can be easily reformed for its hydrogen content and can be distributed through existing gas stations in the purity required for either fuel cells or vehicles.

The following definitions and abbreviations are to be used for the interpretation of the claims and the specification.

The term "invention" or "present invention" as used herein is meant to apply generally to all embodiments of the invention as described in the claims as presented or as later amended and supplemented, or in the specification.

The term "isobutanol biosynthetic pathway" refers to the enzymatic pathway to produce isobutanol. Preferred isobutanol biosynthetic pathways are illustrated in FIG. 1 and described herein.

The term "NADPH consumption assay" refers to an enzyme assay for the determination of the specific activity of the KARI enzyme, involving measuring the disappearance of the KARI cofactor, NADPH, from the enzyme reaction, as described in (Aulabaugh et al.; *Biochemistry*, 29, 2824-2830, 1990).

"KARI" is the abbreviation for the enzyme Ketol-acid reductoisomerase.

The term "Acetohydroxy acid isomeroreductase" and "Ketol-acid reductoisomerase" will be used interchangeably and refer the enzyme having the EC number, EC 1.1.1.86 (*Enzyme Nomenclature* 1992, Academic Press, San Diego). Ketol-acid reductoisomerase catalyzes the reaction of (S)-acetolactate to 2,3-dihydroxyisovalerate, as more fully described below. These enzymes are available from a number of sources, including, but not limited to *E. coli* GenBank Accession Number NC_000913 REGION: 3955993.3957468, *Vibrio cholerae* GenBank Accession Number NC_002505 REGION: 157441.158925, *Pseudomonas aeruginosa*, GenBank Accession Number NC_002516 REGION: 5272455.5273471, and *Pseudomonas fluorescens* GenBank Accession Number NC_004129 REGION: 6017379.6018395.

The term "acetolactate synthase" refers to an enzyme that catalyzes the conversion of pyruvate to acetolactate and $CO_2$. Acetolactatehas two, (R)- and (S)-stereoisomers, the enzyme prefers the (S)-isomer which is made by biological systems. Preferred acetolactate synthases are known by the EC number 2.2.1.6 9 (*Enzyme Nomenclature* 1992, Academic Press, San Diego). These enzymes are available from a number of sources, including, but not limited to, *Bacillus subtilis* (GenBank Nos: CAB15618, Z99122, NCBI (National Center for Biotechnology Information) amino acid sequence, NCBI nucleotide sequence, respectively), *Klebsiella pneumoniae* (GenBank Nos: AAA25079 (SEQ ID NO:2), M73842 (SEQ ID NO:1)), and *Lactococcus lactis* (GenBank Nos: AAA25161, L16975).

The term "acetohydroxy acid dehydratase" refers to an enzyme that catalyzes the conversion of 2,3-dihydroxyisovalerate to α-ketoisovalerate. Preferred acetohydroxy acid dehydratases are known by the EC number 4.2.1.9. These enzymes are available from a vast array of microorganisms, including, but not limited to, *E. coli* (GenBank Nos: YP_026248 (SEQ ID NO:6), NC_000913 (SEQ ID NO:5)), *S. cerevisiae* (GenBank Nos: NP_012550, NC_001142), *M. maripaludis* (GenBank Nos: CAF29874, BX957219), and *B. subtilis* (GenBank Nos: CAB14105, Z99115).

The term "branched-chain α-keto acid decarboxylase" refers to an enzyme that catalyzes the conversion of α-ketoisovalerate to isobutyraldehyde and $CO_2$. Preferred branched-chain α-keto acid decarboxylases are known by the EC number 4.1.1.72 and are available from a number of sources, including, but not limited to, *Lactococcus lactis* (GenBank Nos: AAS49166, AY548760; CAG34226 (SEQ ID NO:8), AJ746364, *Salmonella typhimurium* (GenBank Nos: NP_461346, NC_003197), and *Clostridium acetobutylicum* (GenBank Nos: NP_149189, NC_001988).

The term "branched-chain alcohol dehydrogenase" refers to an enzyme that catalyzes the conversion of isobutyraldehyde to isobutanol. Preferred branched-chain alcohol dehydrogenases are known by the EC number 1.1.1.265, but may also be classified under other alcohol dehydrogenases (specifically, EC 1.1.1.1 or 1.1.1.2). These enzymes utilize NADH (reduced nicotinamide adenine dinucleotide) and/or NADPH as electron donor and are available from a number of sources, including, but not limited to, *S. cerevisiae* (GenBank Nos: NP_010656, NC_001136; NP_014051, NC_001145), *E. coli* (GenBank Nos: NP_417484 (SEQ ID NO:10), NC_000913 (SEQ ID NO:9)), and *C. acetobutylicum* (GenBank Nos: NP_349892, NC_003030).

The term "branched-chain keto acid dehydrogenase" refers to an enzyme that catalyzes the conversion of α-ketoisovalerate to isobutyryl-CoA (isobutyryl-coenzyme A), using $NAD^+$ (nicotinamide adenine dinucleotide) as electron acceptor. Preferred branched-chain keto acid dehydrogenases are known by the EC number 1.2.4.4. These branched-chain keto acid dehydrogenases are comprised of four subunits and sequences from all subunits are available from a vast array of microorganisms, including, but not limited to, *B. subtilis* (GenBank Nos: CAB14336, Z99116; CAB14335, Z99116; CAB14334, Z99116; and CAB14337, Z99116) and *Pseudomonas putida* (GenBank Nos: AAA65614, M57613; AAA65615, M57613; AAA65617, M57613; and AAA65618, M57613).

The term "carbon substrate" or "fermentable carbon substrate" refers to a carbon source capable of being metabolized by host organisms of the present invention and particularly carbon sources selected from the group consisting of monosaccharides, oligosaccharides, polysaccharides, and one-carbon substrates or mixtures thereof.

The terms "$k_{cat}$" and "$K_m$" are known to those skilled in the art and are described in Enzyme Structure and Mechanism, $2^{nd}$ ed. (Ferst; W.H. Freeman: NY, 1985; pp 98-120). The term "$k_{cat}$", often called the "turnover number", is defined as the maximum number of substrate molecules converted to products per active site per unit time, or the number of times the enzyme turns over per unit time. $k_{cat}=Vmax/[E]$, where [E] is the enzyme concentration (Ferst, supra). The terms "total turnover" and "total turnover number" are used herein to refer to the amount of product formed by the reaction of a KARI enzyme with substrate.

The term "catalytic efficiency" is defined as the $k_{cat}/K_M$ of an enzyme. "Catalytic efficiency" is used to quantitate the specificity of an enzyme for a substrate.

The term "specific activity" means enzyme units/mg protein where an enzyme unit is defined as moles of product formed/minute under specified conditions of temperature, pH, [S], etc.

The term "slow" or "fast" when used in reference to an enzyme activity relates to the turnover number of the enzyme as compares with a standard.

The term "isolated nucleic acid molecule", "isolated nucleic acid fragment" and "genetic construct" will be used interchangeably and will mean a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "Gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein the term "Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

As used herein the term "transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

As used herein the term "Codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

Standard recombinant DNA and molecular cloning techniques used here are well known in the art and are described by Sambrook et al. (Sambrook, Fritsch, and Maniatis, *Molecular Cloning: A Laboratory Manual*, Second Edition, Cold Spring Harbor Laboratory Press, Cold Spring Harbor, N.Y., 1989) (hereinafter "Maniatis"); and by Silhavy et al. (Silhavy, et al., *Experiments with Gene Fusions*, Cold Spring Harbor Laboratory Press Cold Spring Harbor, N.Y., 1984); and by Ausubel, F. M. et al., (Ausubel, et al, *Current Protocols in Molecular Biology*, published by Greene Publishing Assoc. and Wiley-Interscience, 1987).

The present invention produces isobutanol from plant derived carbon sources, avoiding the negative environmental impact associated with standard petrochemical processes for butanol production. In one embodiment the present invention provides a method for identification of KARI enzymes with high catalytic efficiency which would eliminate it as the rate limiting step in the conversion of carbohydrates to isobutanol. The method comprises identification and suitable KARI enzymes and their mutagenesis using methods well known in the art to increase the enzyme's specific activity as described in detail below.

Keto Acid Reductoisomerase (KARI) Enzymes

Acetohydroxy acid isomeroreductase or Ketol-acid reductoisomerase (KARI; EC 1.1.1.86) catalyzes 2 steps in the biosynthesis of branched-chain amino acids and is a key enzyme in their biosynthesis. KARI is found in a variety of organisms and amino acid sequence comparisons across species have revealed that there are 2 types of this enzyme: a short form (class I) found in fungi and most bacteria, and a long form (class II) typical of plants.

The short form KARIs have typically between 330-340 amino acid residues. The long form KARI have about 490 amino acid residues. However, some bacteria such as *Escherichia coli* possess a long form, where the amino acid sequence differs appreciably from that found in plants. KARI is encoded by the ilvC gene and is an essential enzyme for growth of *E. coli* and other bacteria in a minimal medium. KARI uses NADPH as cofactor and requires divalent cation such as $Mg^{++}$ for its activity. In addition to utilizing acetolactate in the valine pathway, KARI also converts acetohydroxybutanoate to dihydroxymethylpentanoate in the isoleucine production pathway.

The crystal structure of the *E. coli* KARI enzyme at 2.6 Å resolution has been solved (Tyagi, et al., *Protein Science*, 14, 3089-3100, 2005). This enzyme consists of 2 domains, one with mixed α/β structure, which is similar to that found in other pyridine nucleotide-dependent dehydrogenases. The 2nd domain is mainly α-helical and shows strong evidence of internal duplication. Comparison of the active sites of KARI of *E. coli, Pseudomonas aeruginosa,* and spinach showed that most residues in the active site of the enzyme occupy conserved positions. While the *E. coli* KARI was crystallized as a tetramer, which is probably the likely biologically active unit, the *P. aeruginosa* KARI (Ahn, et al., *J. Mol. Biol.,* 328, 505-515, 2003) formed a dodecamer, and the enzyme from spinach formed a dimer. Known KARIs are slow enzymes with the reported turnover number ($k_{cat}$) of 2 $s^{-1}$ (Aulabaugh et al.; *Biochemistry,* 29, 2824-2830, 1990) or 0.12 $s^{-1}$ (Rane et al., *Arch. Biochem. Biophys.* 338, 83-89, 1997) for acetolactate. Studies have shown that genetic control of isoleucine-valine biosynthesis in *E. coli* is different than that in *Ps. aeruginosa* (Marinus, et al., *Genetics,* 63, 547-56, 1969).

Identification and Isolation of High Activity KARI Enzymes.

A review of organisms with higher doubling rates than *E. coli* was performed. Three microorganisms, *Pseudomonas aeruginosa* (PAO1), *Pseudomonas fluorescens* (PF5), and *Vibrio cholerae* (N16961), were identified which had faster doubling times than *E. coli* when grown in the M9 minimal medium. Genes encoding a KARI enzyme were isolated from each of these varieties and the encoded proteins were expressed and partially purified. The specific activity of the enzymes isolated from the high doubling rate organisms was compared against that of the *E. coli.* KARI, using the NADPH consumption assay method which measures the disappearance of the cofactor, NADPH, during the enzymatic conversion of acetolactate to α,β-dihydroxy-isovalerate at 340 nm. The activity is calculated using the molar extinction coefficient of 6220 $M^{-1}cm^{-1}$ for NADPH and is reported as μmole of NADPH consumed per min per mg of total protein in cell extracts (see Aulabaugh and Schloss, *Biochemistry,* 29, 2824-2830, 1990)

It is an object of the present invention to provide a KARI enzyme having a specific activity of greater than 1.1 μmoles/min/mg KARI as measured using purified protein according to the NADPH consumption assay described herein. *E. coli* KARI is a slow enzyme and is essential in branch chain amino acid synthetic pathway. The gene that encodes KARI (ilvC) is turned off when cells grow in a rich medium but it is expressed at high levels (about 10% of the soluble proteins) when grown in a minimal medium (S. Epelbaum et al., supra).

The process of the selection of a suitable KARI enzyme involved two approaches. The first was to search for a novel KARI among natural diversity. Such a search involved isolating homologues to available enzymes broadly from other organisms, using techniques well-known in the art. This search was informed by hypotheses about which organisms are most likely to have suitable KARIs, based on the doubling time of the organism. A second approach involved creating and searching artificial diversity by construction of a strong expression vector, mutagenesis and evolution of the KARI coding sequence, and finally selection of variants with improved KARI activity.

Using the above methods, KARI enzymes were isolated from *Pseudomonas aeruginosa* (SEQ ID No. 35 [PAO1-ilvC], *Pseudomonas fluorescens* (SEQ ID No. 36 [PF5-ilvC]) and *Vibrio cholerae* (SEQ ID No. 34) having a specific activities that were higher than that of the KARI enzyme isolated from *E. coli* (SEQ ID No. 33 [*E. coli* K12-ilvC].

Preferred in the present invention are KARI enzymes having specific activities of greater than about 1.1 μmoles/min/mg, where specific activities, of about 5-40 μmoles/min/mg are particularly suitable. It is preferable if the specific activity of the KARI is measured using purified protein and incorporating a NADPH consumption assay (Aulabaugh, supra) run at between 20° C. and 25° C., where about 22.5° C. is preferred, at a pH of between 7.0 and 8.0, where a pH of about 7.5 is preferred, and in a buffer having at least about 10 mM potassium, where at least about 10 mM-to about 50 mM is suitable. Some of the specific enzymes useful in the invention are listed below in Table 2.

TABLE 2

KARI Enzymes of the Present Invention

| Gene | GenBank citation |
| --- | --- |
| *E. coli* K12 ilvC | GenBank Accession Number NC_000913 REGION: 3955993 ... 3957468 |
| Codon optimized for *E. coli* expression of KARI from *Vibrio cholerae* | GenBank Accession Number NC_002505 REGION: 157441 ... 158925 |
| *Pseudomonas aeruginosa* PAO1 ilvC | GenBank Accession Number NC_002516 REGION: 5272455 ... 5273471 |
| *Pseudomonas fluorescens* PF5 ilvC | GenBank Accession Number NC_004129 REGION: 6017379 ... 6018395 |

The present invention is not limited to the specific *Pseudomonas* and *Vibrio* enzymes described herein. For example, these polypeptides may be used as the basis to find homologs having similar activity, or as templates for mutagenesis and protein evolution.

Isolation of KARI Homologs

The nucleic acid fragment of the instant invention may be used to isolate genes encoding homologous proteins from the same or other microbial species. Isolation of homologous KARI genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies, e.g. polymerase chain reaction (PCR) (Mullis et al., U.S. Pat. No. 4,683,202), ligase chain reaction (LCR), (Tabor, et al., *Proc. Acad. Sci*. USA 82, 1074, 1985) or strand displacement amplification (SDA) (Walker, et al., *Proc. Natl. Acad. Sci. U.S.A.,* 89, 392, 1992).

For example, genes encoding similar proteins or polypeptides to those of the instant invention could be isolated directly by using all or a portion of the instant nucleic acid fragment as DNA hybridization probes to screen libraries from any desired bacteria using methodology well known to those skilled in the art. Specific oligonucleotide probes based upon the instant nucleic acid sequence can be designed and synthesized by methods known in the art (Maniatis, supra). Moreover, the entire sequence can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or the full-length of the instant sequence. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art, e.g. Thein et al (Thein et al., "The use of oligonucleotide as specific hybridization probes in the Diagnosis of Genetic Disorders", in *Human Genetic Diseases: A Practical Approach*, K. E. Davis Ed., 1986, pp. 33-50 IRL Press, Herndon, Va.); and Rychlik (Rychlik, 1993, In White, B. A. (ed.), *Methods in Molecular Biology*, Vol. 15, pages 31-39, PCR Protocols: Current Methods and Applications. Humana Press, Inc., Totowa, N.J.)

Generally two short segments of the instant sequence may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragment, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *Proc. Natl. Acad. Sci. USA,* 85, 8998, 1988) to generate cDNAs by using PCR to amplify copies of the region between a single point in the transcript and the 3' or 5' end. Primers oriented in the 3' and 5' directions can be designed from the instant sequence. Using commercially available 3' RACE or 5' RACE systems (Life Technologies, Rockville, Md.), specific 3' or 5' cDNA fragments can be isolated (Ohara et al., *Proc. Natl. Acad. Sci. USA,* 86, 5673, 1989); and (Loh et al., *Science,* 243, 217-220 1989).

Alternatively the instant sequence may be employed as a hybridization reagent for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness et al., *Nucl. Acids Res.* 19, 5143-5151, 1991). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1.0 M sodium chloride, about 0.05 to 0.1M buffers, such as sodium citrate, Tris-HCl, PIPES or HEPES (pH range about 6-9), about 0.05 to 0.2% detergent, such as sodium dodecylsulfate, or between 0.5-20 mM EDTA, FICOLL (Pharmacia Inc.) (about 300-500 kiloDaltons), polyvinylpyrrolidone (about 250-500 kiloDaltons), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% w/v glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Isobutanol Biosynthetic Pathways

One of the principal uses of the present high activity KARI enzymes will be as an element in metabolic pathways useful for the production of isobutanol. A number of these pathways have been elucidated and characterized.

Carbohydrate utilizing microorganisms employ the Embden-Meyerhof-Parnas (EMP) pathway, the Entner and Doudoroff pathway and the pentose phosphate cycle as the central, metabolic routes to provide energy and cellular precursors for growth and maintenance. These pathways have in common the intermediate glyceraldehyde-3-phosphate and, ultimately, pyruvate is formed directly or in combination with the EMP pathway. Subsequently, pyruvate is transformed to acetyl-coenzyme A (acetyl-CoA) via a variety of means. Acetyl-CoA serves as a key intermediate, for example, in generating fatty acids, amino acids and secondary metabolites. The combined reactions of sugar conversion to pyruvate produce energy (e.g. adenosine-5'-triphosphate, ATP) and reducing equivalents (e.g. reduced nicotinamide adenine dinucleotide, NADH, and reduced nicotinamide adenine dinucleotide phosphate, NADPH). NADH and NADPH must be recycled to their oxidized forms (NAD$^+$ and NADP$^+$, respectively). In the presence of inorganic electron acceptors (e.g. $O_2$, $NO_3^-$ and $SO_4^{2-}$), the reducing equivalents may be used to augment the energy pool; alternatively, a reduced carbon byproduct may be formed.

There are four potential pathways for production of isobutanol from carbohydrate sources with recombinant microorganisms as shown in FIG. 1. All potential pathways for conversion of carbohydrates to isobutanol have been described in the commonly owned U.S. patent application Ser. No. 11/586,315, which is incorporated herein by reference.

The preferred pathway for conversion of pyruvate to isobutanol consists of enzymatic steps "a", "b", "c", "d", and "e" (FIG. 1) and includes the following substrate to product conversions:

a) pyruvate to acetolactate, as catalyzed for example by acetolactate synthase, b) (S)-acetolactate to 2,3-dihydroxyisovalerate, as catalyzed for example by acetohydroxy acid isomeroreductase, c) 2,3-dihydroxyisovalerate to α-ketoisovalerate, as catalyzed for example by acetohydroxy acid dehydratase, d) α-ketoisovalerate to isobutyraldehyde, as catalyzed for example by a branched-chain keto acid decarboxylase, and e) isobutyraldehyde to isobutanol, as catalyzed for example by, a branched-chain alcohol dehydrogenase.

This pathway combines enzymes involved in well-characterized pathways for valine biosynthesis (pyruvate to α-ketoisovalerate) and valine catabolism (α-ketoisovalerate to isobutanol). Since many valine biosynthetic enzymes also catalyze analogous reactions in the isoleucine biosynthetic pathway, substrate specificity is a major consideration in selecting the gene sources. For this reason, the primary genes of interest for the acetolactate synthase enzyme are those from *Bacillus* (alsS) and *Klebsiella* (budB). These particular acetolactate synthases are known to participate in butanediol fermentation in these organisms and show increased affinity for pyruvate over ketobutyrate (Gollop et al., *J. Bacteriol.* 172, 3444-3449, 1990); and (Holtzclaw et al., *J. Bacteriol.* 121, 917-922, 1975). The second and third pathway steps are catalyzed by acetohydroxy acid reductoisomerase and dehydratase, respectively. These enzymes have been characterized from a number of sources, such as for example, *E. coli* (Chunduru et al., *Biochemistry* 28, 486-493, 1989); and (Flint et al., *J. Biol. Chem.* 268, 14732-14742, 1993). The final two steps of the preferred isobutanol pathway are known to occur in yeast, which can use valine as a nitrogen source and, in the process, secrete isobutanol. α-Ketoiso-valerate can be converted to isobutyraldehyde by a number of keto acid decarboxylase enzymes, such as for example pyruvate decarboxylase. To prevent misdirection of pyruvate away from isobutanol production, a decarboxylase with decreased affinity for pyruvate is desired. So far, there are two such enzymes known in the art (Smit et al., *Appl. Environ. Microbiol.* 71, 303-311, 2005); and (de la Plaza et al., *FEMS Microbiol. Lett.* 238, 367-374, 2004). Both enzymes are from strains of *Lactococcus lactis* and have a 50-200-fold preference for ketoisovalerate over pyruvate. Finally, a number of aldehyde reductases have been identified in yeast, many with overlapping substrate specificity. Those known to prefer branched-chain substrates over acetaldehyde include, but are not limited to, alcohol dehydrogenase VI (ADH6) and Ypr1p (Larroy et al., *Biochem. J.* 361, 163-172, 2002); and (Ford et al., Yeast 19, 1087-1096, 2002), both of which use NADPH as electron donor. An NADPH-dependent reductase, YqhD, active with branched-chain substrates has also been recently identified in *E. coli* (Sulzenbacher et al., *J. Mol. Biol.* 342, 489-502, 2004).

Two of the other potential pathways for isobutanol production also contain the initial three steps of "a", "b" and "c". One pathway consists of enzymatic steps "a", "b", "c", "f", "g", "e". Step "f" containing a "branched-chain keto acid dehydrogenase" with an EC number 1.2.4.4. Step "g" containing an "acylating aldehyde dehydrogenase" with a EC numbers 1.2.1.10 and 1.2.1.57 in addition to step "e" containing the "branched chain alcohol dehydrogenase". The other potential pathway consists of steps "a", "b", "c", "h", "i", "j", "e". The term "transaminase" (step "h") EC numbers 2.6.1.42 and 2.6.1.66. Step "h" consists of either a "valine dehydrogenase" with EC numbers 1.4.1.8 and 1.4.1.9 or step "i", a "valine decarboxylase" with an EC number 4.1.1.14. Finally step "j" will use an "omega transaminase" with an EC number 2.6.1.18 to generate isobutyraldehyde which will be reduced by step "e" to produce isobutanol. All potential pathways for conversion of pyruvate to isobutanol are depicted in FIG. 1.

Additionally, a number of organisms are known to produce butyrate and/or butanol via a butyryl-CoA intermediate (Dürre et al., *FEMS Microbiol. Rev.* 17, 251-262, 1995); and (Abbad-Andaloussi et al., *Microbiology* 142, 1149-1158, 1996). Therefore isobutanol production in these organisms will take place using steps "k", "g" and "e" shown in FIG. 1. Step "k" will use an "isobutyryl-CoA mutase" with an EC number 5.4.99.13. The nest step will involve using the "acylating aldehyde dehydrogenase" with the EC numbers 1.2.1.10 and 1.2.1.57 to produce isobutyraldehyde followed by enzymatic step "e" to produce isobutanol. All these pathways are fully described in the commonly owned U.S. patent application Ser. No. 11/586,315 herein incorporated by reference in its entirety.

Microbial Hosts for Isobutanol Production

Microbial hosts for isobutanol production may be selected from bacteria, cyanobacteria, filamentous fungi and yeasts. The microbial host used for isobutanol production should be tolerant to isobutanol so that the yield is not limited by butanol toxicity. Microbes that are metabolically active at high titer levels of isobutanol are not well known in the art. Although butanol-tolerant mutants have been isolated from solventogenic Clostridia, little information is available concerning the butanol tolerance of other potentially useful bacterial strains. Most of the studies on the comparison of alcohol tolerance in bacteria suggest that butanol is more toxic than ethanol (de Cavalho et al., *Microsc. Res. Tech.* 64, 215-22, 2004) and (Kabelitz et al., *FEMS Microbiol. Lett.* 220, 223-227, 2003, Tomas et al. *J. Bacteriol.* 186, 2006-2018, 2004) report that the yield of 1-butanol during fermentation in *Clostridium acetobutylicum* may be limited by 1-butanol toxicity. The primary effect of 1-butanol on *Clostridium acetobutylicum* is disruption of membrane functions (Hermann et al., *Appl. Environ. Microbiol.* 50, 1238-1243, 1985).

The microbial hosts selected for the production of isobutanol should be tolerant to isobutanol and should be able to convert carbohydrates to isobutanol. The criteria for selection of suitable microbial hosts include the following: intrinsic tolerance to isobutanol, high rate of glucose utilization, availability of genetic tools for gene manipulation, and the ability to generate stable chromosomal alterations.

Suitable host strains with a tolerance for isobutanol may be identified by screening based on the intrinsic tolerance of the strain. The intrinsic tolerance of microbes to isobutanol may be measured by determining the concentration of isobutanol that is responsible for 50% inhibition of the growth rate ($IC_{50}$) when grown in a minimal medium. The $IC_{50}$ values may be determined using methods known in the art. For example, the microbes of interest may be grown in the presence of various amounts of isobutanol and the growth rate monitored by measuring the optical density at 600 nanometers ($OD_{600}$). The doubling time may be calculated from the logarithmic part of the growth curve and used as a measure of the growth rate. The concentration of isobutanol that produces 50% inhibition of growth may be determined from a graph of the percent inhibition of growth versus the isobutanol concentration. Preferably, the host strain should have an $IC_{50}$ for isobutanol of greater than about 0.5%.

The microbial host for isobutanol production should also utilize glucose at a high rate. Most microbes are capable of utilizing carbohydrates. However, certain environmental microbes cannot utilize carbohydrates to high efficiency, and therefore would not be suitable hosts.

The ability to genetically modify the host is essential for the production of any recombinant microorganism. The mode of gene transfer technology may be by electroporation, conjugation, transduction or natural transformation. A broad range of host conjugative plasmids and drug resistance markers are available. The cloning vectors are tailored to the host organisms based on the nature of antibiotic resistance markers that can function in that host.

The microbial host also has to be manipulated in order to inactivate competing pathways for carbon flow by deleting various genes. This requires the availability of either transposons to direct inactivation or chromosomal integration vectors. Additionally, the production host should be amenable to chemical mutagenesis so that mutations to improve intrinsic isobutanol tolerance may be obtained.

Based on the criteria described above, suitable microbial hosts for the production of isobutanol include, but are not limited to, members of the genera *Clostridium, Zymomonas, Escherichia, Salmonella, Rhodococcus, Pseudomonas, Bacillus, Vibrio, Lactobacillus, Enterococcus, Alcaligenes, Klebsiella, Paenibacillus, Arthrobacter, Corynebacterium, Brevibacterium, Pichia, Candida, Hansenula* and *Saccharomyces*. Preferred hosts include: *Escherichia coli, Alcaligenes eutrophus, Bacillus licheniformis, Paenibacillus macerans, Rhodococcus erythropolis, Pseudomonas putida, Lactobacillus plantarum, Enterococcus faecium, Enterococcus gallinarium, Enterococcus faecalis, Bacillus subtilis* and *Saccharomyces cerevisiae*.

Construction of Production Host

Recombinant organisms containing the necessary genes that will encode the enzymatic pathway for the conversion of a fermentable carbon substrate to isobutanol may be constructed using techniques well known in the art. In the present invention, genes encoding the enzymes of one of the isobutanol biosynthetic pathways of the invention, for example, acetolactate synthase, acetohydroxy acid isomeroreductase, acetohydroxy acid dehydratase, branched-chain α-keto acid decarboxylase, and branched-chain alcohol dehydrogenase, may be isolated from various sources, as described above.

Methods of obtaining desired genes from a bacterial genome are common and well known in the art of molecular biology. For example, if the sequence of the gene is known, suitable genomic libraries may be created by restriction endonuclease digestion and may be screened with probes complementary to the desired gene sequence. Once the sequence is isolated, the DNA may be amplified using standard primer-directed amplification methods such as polymerase chain reaction (U.S. Pat. No. 4,683,202) to obtain amounts of DNA suitable for transformation using appropriate vectors. Tools for codon optimization for expression in a heterologous host are readily available. Some tools for codon optimization are available based on the GC content of the host organism.

Once the relevant pathway genes are identified and isolated they may be transformed into suitable expression hosts by means well known in the art. Vectors or cassettes useful for the transformation of a variety of host cells are common and commercially available from companies such as EPICENTRE® (Madison, Wis.), Invitrogen Corp. (Carlsbad, Calif.), Stratagene (La Jolla, Calif.), and New England Biolabs, Inc. (Beverly, Mass.). Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. Both control regions may be derived from genes homologous to the transformed host cell, although it is to be understood that such control regions may also be derived from genes that are not native to the specific species chosen as a production host.

Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli, Alcaligenes*, and *Pseudomonas*) as well as the amy, apr, npr promoters and various phage promoters useful for expression in *Bacillus subtilis, Bacillus licheniformis*, and *Paenibacillus macerans*.

Termination control regions may also be derived from various genes native to the preferred hosts. Optionally, a termination site may be unnecessary, however, it is most preferred if included.

Certain vectors are capable of replicating in a broad range of host bacteria and can be transferred by conjugation. The complete and annotated sequence of pRK404 and three related vectors-pRK437, pRK442, and pRK442(H) are available. These derivatives have proven to be valuable tools for genetic manipulation in Gram-negative bacteria (Scott et al., *Plasmid* 50, 74-79, 2003). Several plasmid derivatives of broad-host-range Inc P4 plasmid RSF1010 are also available with promoters that can function in a range of Gram-negative bacteria. Plasmid pAYC36 and pAYC37, have active promoters along with multiple cloning sites to allow for the heterologous gene expression in Gram-negative bacteria.

Chromosomal gene replacement tools are also widely available. For example, a thermosensitive variant of the broad-host-range replicon pWV101 has been modified to construct a plasmid pVE6002 which can be used to effect gene replacement in a range of Gram-positive bacteria (Maguin et al., *J. Bacteriol.* 174, 5633-5638, 1992). Additionally, in vitro transposomes are available to create random mutations in a variety of genomes from commercial sources such as EPICENTRE®.

The expression of an isobutanol biosynthetic pathway in various preferred microbial hosts is described in more detail below.

Expression of an Isobutanol Biosynthetic Pathway in *E. coli*

Vectors or cassettes useful for the transformation of *E. coli* are common and commercially available from the companies listed above. For example, the genes of an isobutanol biosynthetic pathway may be isolated from various sources, cloned into a modified pUC19 vector and transformed into *E. coli* NM522.

Expression of an Isobutanol Biosynthetic Pathway in *Rhodococcus erythropolis*

A series of *E. coli-Rhodococcus* shuttle vectors are available for expression in *R. erythropolis*, including, but not limited to, pRhBR17 and pDA71 (Kostichka et al., *Appl. Microbiol. Biotechnol.* 62, 61-68, 2003). Additionally, a series of promoters are available for heterologous gene expression in *R. erythropolis* (Nakashima et al., *Appl. Environ. Microbiol.* 70, 5557-5568, 2004 and Tao et al., *Appl. Microbiol. Biotechnol.* 68, 346-354, 2005). Targeted gene disruption of chromosomal genes in *R. erythropolis* may be created using the method described by Tao et al., supra, and Brans et al. (*Appl. Environ. Microbiol.* 66, 2029-2036, 2000).

The heterologous genes required for the production of isobutanol, as described above, may be cloned initially in pDA71 or pRhBR71 and transformed into *E. coli*. The vectors may then be transformed into *R. erythropolis* by electroporation, as described by Kostichka et al., supra. The recombinants may be grown in synthetic medium containing glucose and the production of isobutanol can be followed using methods known in the art.

Expression of an Isobutanol Biosynthetic Pathway in *B. subtilis*

Methods for gene expression and creation of mutations in *B. subtilis* are also well known in the art. For example, the genes of an isobutanol biosynthetic pathway may be isolated from various sources, cloned into a modified pUC19 vector and transformed into *Bacillus subtilis* BE1010. Additionally, the five genes of an isobutanol biosynthetic pathway can be split into two operons for expression. The three genes of the pathway (bubB, ilvD, and kivD) can be integrated into the chromosome of *Bacillus subtilis* BE1010 (Payne, et al., *J. Bacteriol.* 173, 2278-2282, 1991). The remaining two genes (ilvC and bdhB) can be cloned into an expression vector and transformed into the *Bacillus* strain carrying the integrated isobutanol genes Expression of an Isobutanol Biosynthetic Pathway in *B. licheniformis*

Most of the plasmids and shuttle vectors that replicate in *B. subtilis* may be used to transform *B. licheniformis* by either protoplast transformation or electroporation. The genes required for the production of isobutanol may be cloned in plasmids pBE20 or pBE60 derivatives (Nagarajan et al., *Gene* 114, 121-126, 1992). Methods to transform *B. licheniformis* are known in the art (Fleming et al. *Appl. Environ. Microbiol.*, 61, 3775-3780, 1995). The plasmids constructed for expression in *B. subtilis* may be transformed into *B. licheniformis* to produce a recombinant microbial host that produces isobutanol.

Expression of an Isobutanol Biosynthetic Pathway in *Paenibacillus macerans*

Plasmids may be constructed as described above for expression in *B. subtilis* and used to transform *Paenibacillus macerans* by protoplast transformation to produce a recombinant microbial host that produces isobutanol.

Expression of the Isobutanol Biosynthetic Pathway in *Alcaligenes* (*Ralstonia*) *eutrophus*

Methods for gene expression and creation of mutations in *Alcaligenes eutrophus* are known in the art (Taghavi et al., *Appl. Environ. Microbiol.*, 60, 3585-3591, 1994). The genes for an isobutanol biosynthetic pathway may be cloned in any of the broad host range vectors described above, and electroporated to generate recombinants that produce isobutanol. The poly(hydroxybutyrate) pathway in *Alcaligenes* has been described in detail, a variety of genetic techniques to modify the *Alcaligenes eutrophus* genome is known, and those tools can be applied for engineering an isobutanol biosynthetic pathway.

Expression of an Isobutanol Biosynthetic Pathway in *Pseudomonas putida*

Methods for gene expression in *Pseudomonas putida* are known in the art (see for example Ben-Bassat et al., U.S. Pat. No. 6,586,229, which is incorporated herein by reference). The butanol pathway genes may be inserted into pPCU18 and this ligated DNA may be electroporated into electrocompetent *Pseudomonas putida* DOT-T1 C5aAR1 cells to generate recombinants that produce isobutanol.

Expression of an Isobutanol Biosynthetic Pathway in *Saccharomyces cerevisiae*

Methods for gene expression in *Saccharomyces cerevisiae* are known in the art (e.g., *Methods in Enzymology*, Volume 194, *Guide to Yeast Genetics and Molecular and Cell Biology, Part A*, 2004, Christine Guthrie and Gerald R. Fink, eds., Elsevier Academic Press, San Diego, Calif.). Expression of genes in yeast typically requires a promoter, followed by the gene of interest, and a transcriptional terminator. A number of yeast promoters can be used in constructing expression cassettes for genes encoding an isobutanol biosynthetic pathway, including, but not limited to constitutive promoters FBA, GPD, ADH1, and GPM, and the inducible promoters GAL1, GAL10, and CUP1. Suitable transcriptional terminators include, but are not limited to FBAt, GPDt, GPMt, ERG10t, GAL1t, CYC1, and ADH1. For example, suitable promoters, transcriptional terminators, and the genes of an isobutanol biosynthetic pathway may be cloned into E. coli-yeast shuttle vectors.

Expression of an Isobutanol Biosynthetic Pathway in Lactobacillus plantarum

The Lactobacillus genus belongs to the Lactobacillales family and many plasmids and vectors used in the transformation of Bacillus subtilis and Streptococcus may be used for lactobacillus. Non-limiting examples of suitable vectors include pAMβ1 and derivatives thereof (Renault et al., Gene 183, 175-182, 1996); and (O'Sullivan et al., Gene 137, 227-231, 1993); pMBB1 and pHW800, a derivative of pMBB1 (Wyckoff et al. Appl. Environ. Microbiol. 62, 1481-1486, 1996); pMG1, a conjugative plasmid (Tanimoto et al., J. Bacteriol. 184, 5800-5804, 2002); pNZ9520 (Kleerebezem et al., Appl. Environ. Microbiol. 63, 4581-4584, 1997); pAM401 (Fujimoto et al., Appl. Environ. Microbiol. 67, 1262-1267, 2001); and pAT392 (Arthur et al., Antimicrob. Agents Chemother. 38, 1899-1903, 1994). Several plasmids from Lactobacillus plantarum have also been reported (van Kranenburg R, et al. Appl. Environ. Microbiol. 71, 1223-1230, 2005).

Expression of an Isobutanol Biosynthetic Pathway in Various Enterococcus Species (E. faecium, E. gallinarium, and E. faecalis)

The Enterococcus genus belongs to the Lactobacillales family and many plasmids and vectors used in the transformation of Lactobacilli, Bacilli and Streptococci species may be used for Enterococcus species. Non-limiting examples of suitable vectors include pAMβ1 and derivatives thereof (Renault et al., Gene 183, 175-182, 1996); and (O'Sullivan et al., Gene 137, 227-231, 1993); pMBB1 and pHW800, a derivative of pMBB1 (Wyckoff et al. Appl. Environ. Microbiol. 62, 1481-1486, 1996); pMG1, a conjugative plasmid (Tanimoto et al., J. Bacteriol. 184, 5800-5804, 2002); pNZ9520 (Kleerebezem et al., Appl. Environ. Microbiol. 63, 4581-4584, 1997); pAM401 (Fujimoto et al., Appl. Environ. Microbiol. 67, 1262-1267, 2001); and pAT392 (Arthur et al., Antimicrob. Agents Chemother. 38, 1899-1903, 1994). Expression vectors for E. faecalis using the nisA gene from Lactococcus may also be used (Eichenbaum et al., Appl. Environ. Microbiol. 64, 2763-2769, 1998). Additionally, vectors for gene replacement in the E. faecium chromosome may be used (Nallaapareddy et al., Appl. Environ. Microbiol. 72, 334-345, 2006)).

Fermentation Media

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, corn steep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., Microb. Growth C1-Compd., [Int. Symp.], 7th (1993), 415-32. (eds): Murrell, J. Collin; Kelly, Don P. Publisher: Intercept, Andover, UK). Similarly, various species of Candida will metabolize alanine or oleic acid (Sulter et al., Arch. Microbiol. 153, 485-489, 1990). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, and sucrose.

In addition to an appropriate carbon source, fermentation media must contain suitable minerals, salts, cofactors, buffers and other components, known to those skilled in the art, suitable for the growth of the cultures and promotion of the enzymatic pathway necessary for isobutanol production.

Culture Conditions

Typically cells are grown at a temperature in the range of about 25° C. to about 40° C. in an appropriate medium. Suitable growth media in the present invention are common commercially prepared media such as Luria Bertani (LB) broth, Sabouraud Dextrose (SD) broth or Yeast Medium (YM) broth. Other defined or synthetic growth media may also be used, and the appropriate medium for growth of the particular microorganism will be known by one skilled in the art of microbiology or fermentation science. The use of agents known to modulate catabolite repression directly or indirectly, e.g., cyclic adenosine 2',3'-monophosphate (cAMP), may also be incorporated into the fermentation medium.

Suitable pH ranges for the fermentation are between pH 5.0 to pH 9.0, where pH 6.0 to pH 8.0 is preferred for the initial condition.

Fermentations may be performed under aerobic or anaerobic conditions, where anaerobic or microaerobic conditions are preferred.

Industrial Batch and Continuous Fermentations

The present process employs a batch method of fermentation. A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund (*Appl. Biochem. Biotechnol.*, 36, 227, 1992), herein incorporated by reference.

Although the present invention is performed in batch mode it is contemplated that the method would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for isobutanol production.

Methods for Isobutanol Isolation from the Fermentation Medium

The biologically produced isobutanol may be isolated from the fermentation medium using methods known in the art for Acetone-butanol-ethanol (ABE) fermentations (see for example, Durre, *Appl. Microbiol. Biotechnol.* 49, 639-648, 1998), and (Groot et al., *Process. Biochem.* 27, 61-75, 1992 and references therein). For example, solids may be removed from the fermentation medium by centrifugation, filtration, decantation and isobutanol may be isolated from the fermentation medium using methods such as distillation, azeotropic distillation, liquid-liquid extraction, adsorption, gas stripping, membrane evaporation, or pervaporation.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described by Sambrook et al (Sambrook, J., Fritsch, E. F. and Maniatis, T. (*Molecular Cloning: A Laboratory Manual*; Cold Spring Harbor Laboratory Press, Cold Spring Harbor, 1989, here in referred to as Maniatis) and Maniatis (supra) and by Silhavy et al, (Silhavy, et al., *Experiments with Gene Fusions*, Cold Spring Harbor Laboratory, Cold Spring Harbor, N.Y. 1984) and by Ausubel et al., (Ausubel et al, *Current Protocols in Molecular Biology*, pub. by Greene Publishing Assoc. and Wiley-Interscience, 1987).

Materials and methods suitable for the maintenance and growth of bacterial cultures are well known in the art. Techniques suitable for use in the following examples may be found as set out in *Manual of Methods for General Bacteriology* (Phillipp et al, eds., American Society for Microbiology, Washington, D.C., 1994) or by Thomas D. Brock in (Brock, *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.) unless otherwise specified.

The oligonucleotide primers to use in the following Examples are given in Table 3.

TABLE 3

OLIGONUCLEOTIDE PRIMERS USED IN THIS INVENTION

| SEQUENCE ID No. | SEQUENCE | Description |
|---|---|---|
| 11 | GAGCTCCTTAAGAAGGAGGTAATCACCATGGCTAACTACTTCAA | Primer for ilvC amplification |
| 12 | GGATCCGATCGAGCTAGCGCGGCCGCTTAACCCGCAACAGCAATACGTTTC | Primer for ilvC amplification |
| 13 | GCTAACAGGAGGAAGAGCTCATGGCACCCTCGCTC | Forward pBAD-SAC1-F |
| 14 | GAGCGAGGGTGCCATGAGCTCTTCCTCCTGTTAGC | Reverse pBAD-SAC1-R |
| 15 | ATCACCGAGCTCATGGCTAACTACTTCAATACACTGAATCTGCG | Forward ilvC-trc-Sac1-F |
| 16 | GGCCGCAAGCTTTTAACCCGCAACAGCAATACGTTTCATATCTGTC | Reverse ilvC-trc-HindIII-R |

TABLE 3-continued

OLIGONUCLEOTIDE PRIMERS USED IN THIS INVENTION

| SEQUENCE ID No. | SEQUENCE | Description |
|---|---|---|
| 17 | CCGTAAAGATATCACCGTAG | ilvC-trc-F3 |
| 18 | CAGTATGAAGGCAAAATCGG | ilvC-trc-F5 |
| 19 | CGTACTCAGCGGTATCAGAG | ilvC-trc-R2 |
| 20 | CAGATTTCACTTCCGCAACG | ilvC-trc-R4 |
| 21 | CGCAACTCTCTACTGTTTCTCCATACCCG | pBAD-e-F1 |
| 22 | ACCGCTTCTGCGTTCTGATTTAATC | PALPK-R1 |
| 23 | CAAAACAGCCAAGCTTTTAGTTCTTGCTCTTGTCGACGATCTTG | PAO1-C-F1 |
| 24 | CAGGAGGAAGAGCTCATGCGCGTTTTCTACGATAAAGACTGTG | PAO1-C-R1 |
| 25 | CAAAACAGCCAAGCTTTTAGTTCTTGGCTTTGTCGACGATTTTG | PF5-C-F1 |
| 26 | CAGGAGGAAGAGCTCATGAAAGTTTTCTACGATAAAGACTGCAC | PF5-C-R1 |
| 27 | GATCATGATCGCGCCGAAGG | PF5-S-F2 |
| 28 | CTGCTCACCGAACAGGTCGG | PF5-S-R2 |
| 37 | CTGCAGCACATGAAGACTCCATGGCACCCTCGCTCGACTCGATCTCGCACTCGTTCGCAAACG | Forward PAL-F1 |
| 38 | TCTCTCATCCGCCAAAACAGAAGCTTCAAGCGAGCATCT | Reverse PAL-R1 |
| 39 | GGGCTAACAGGAGGAAGAATTCATGGCACCCTCGCTCGACTCG | Forward PAL-EcoR1-F1 |
| 40 | CGAGTCGAGCGAGGGTGCCATGAATTCTTCCTCCTGTAGCCC | Reverse PAL-Eco-R1-R1 |

The meaning of abbreviations is as follows: "sec" means second(s), "min" means minute(s), "h" means hour(s), "nm" means nanometers, "uL" means microliter(s), "mL" means milliliter(s), "mg/mL" means milligram per milliliter, "L" means liter(s), "nm" means nanometers, "mM" means millimolar, "M" means molar, "mmol" means millimole(s), "µmole" means micromole(s)", "kg" means kilogram, "g" means gram(s), "µg" means microgram(s) and "ng" means nanogram(s), "PCR" means polymerase chain reaction, "OD" means optical density, "$OD_{600}$" means the optical density measured at a wavelength of 600 nm, "kDa" means kilodaltons, "g" means the gravitation constant, "bp" means base pair(s), "kbp" means kilobase pair(s), "kb" means kilobase, "%" means percent, "% w/v" means weight/volume percent, % v/v" means volume/volume percent, "HPLC" means high performance liquid chromatography, "g/L" means gram per liter, "ug/L" means microgram per liter, 'ng/uL" means nanogram per microliter, "pmol/uL" means picomol per microliter, "RPM" means rotation per minute, "umol/min/mg" means micromole per minute per milligram, "w/v" means weight per volume, "v/v" means volume per volume.

Example 1 (Comparative)

Analysis of KARI Enzyme Activity

This example describes preparation of ilvC gene overexpression constructs and measurement of enzyme activity using the acetolactate dependent oxidation of NADPH by the KARI enzyme encoded by the ilvC gene of E. coli.
Construction of pBAD-ilvC Expression Plasmid—Isolation of the ilvC Gene from E. coli
The ilvC gene coding region was amplified from E. coli strain FM5 (ATCC 53911) genomic DNA using PCR. The cells were grown overnight (37° C., while shaking at 300 RPM) in 50 mL culture tubes containing 4 mL of Luria Bertani (LB) medium (Mediatech Inc., Herndon, Va.). They were then harvested by centrifugation at 1000×g for 3 min and genomic DNA of the cells was prepared using the Gentra Puregene kit (Gentra Systems, Inc., Minneapolis, Minn.; catalog number D-5000A) according to the manufacturer's directions. An ilvC coding region DNA fragment was prepared by PCR using the E. coli DNA as template and primers SEQ ID No: 11 and 12.

PCR was carried out using Finnzymes Phusion™ High-Fidelity PCR Master Mix (New England Biolabs Inc., Beverly, Mass.; catalog no. F-531) according to the manufacturer's protocol. Amplification was carried out in a DNA Thermocycler GeneAmp 9700 (PE Applied Biosystems, Foster city, Calif.). The PCR product (0.5 uL), with no further purification, was ligated into pCR4Blunt TOPO (Invitrogen, Carlsbad, Calif., Cat#45-0031) and transformed into chemically competent TOP10 cells (Invitrogen 44-0301). The ligation product was streaked on a plate containing the LB medium plus 100 ug/mL ampicillin (Teknova Inc, Hollister, Calif., Cat # L1004). Clones containing the ilvC insert were confirmed by restriction digestion with SacI/BamHI. Three out of 4 plasmids digested had the expected 1.5 kbp band. The resulting clone was named pCR4Blunt TOPO-ilvC.

The ilvC fragment from the pCR4Blunt TOPO-ilvC cloning vector was released by SacI/BamHI digestion and ligated into SacI/BamHI digested pTrc99A (Amann, et al., Gene, 69, 301-315, 1988) using T4 DNA ligase (New England Biolabs, Beverly, Mass.). This construct was electroporated into electrocompetent E. coli TOP10 cells (Invitrogen 44-0035), and streaked on an LB/ampicillin plate as described above. The vector containing the 1.5 kb insert was named pTrc99A-ilvC.
Preparation of the pBAD Vector for Cloning
A derivative of the pBAD.HisA (Invitrogen) vector containing a SacI site at the 5'-end of the gene was constructed for cloning the ilvC gene into pBAD using SacI/HindIII restriction sites. This construct was created in three steps. First, the phenylalanine ammonia lyase (PAL; EC 4.3.1.5) coding region from Rhodotorula glutinis was cloned into the pBAD-HisA vector to make pBAD-PAL. Second, the EcoRI site was added at the 5'-end of the gene immediately before the start codon on the pBAD-PAL construct to make pBAD-PAL-EcoRI. Third, the EcoRI site was replaced by a SacI site and the resulting vector was digested with SacI/HindIII to make a pBAD-SacI vector for the cloning of ilvC gene. The PAL gene was first PCR amplified from the pKK223-PAL vector (U.S. Pat. No. 6,521,748) using Forward primer (PAL-F1) (SEQ ID No: 37) and Reverse primer (PAL-R1) (SEQ ID No: 38).

PCR was carried out in a Perkin Elmer PCR9700 thermocycler (PE Applied Biosystems, Foster city, Calif.) using TaKaRa Taq DNA Polymerase Premix (TAKARA Bio USA, Madison, Wis., catalog #TAK_R004A) according to the manufacturer's protocol. The PCR product was partially purified using the QIAQuik PCR purification kit (Qiagen cat #28106) and digested with BbsI and HindIII. This produced a fragment containing an NcoI overhang on the 5' end. The digestion product was then ligated into a pBAD.HisA (Invitrogen) vector that had been digested with NcoI/HindIII. The ligation reaction was carried out using T4 DNA ligase (Promega) by following the standard protocol provided by manufacturer. Two uL of the ligation product were used to transform TOP10 electro-competent cells (Invitrogen) using a Bio-RAD Gene Pulser II (Bio-Rad Laboratories Inc, Hercules, Calif.) by following the manufacturer's directions. The transformed cells were streaked onto agar plates containing the LB medium plus 100 ug/mL ampicillin (Teknova Inc, Hollister, Calif., Cat#L1004) and incubated overnight at 37° C. Clones containing the PAL insert were confirmed by restriction digestion with NcoI/HindIII. This construct was named pBAD-PAL. The EcoRI site was then added to the 5'-end of the PAL gene in the above construct by use of a QuikChange II XL site directed mutagenesis kit (Stratagene, La Jolla Calif., Catalogue #200524). The Forward primer (PAL-EcoRI-F1) (SEQ ID No: 39) and Reverse primer (PAL-EcoR1-R1) (SEQ ID NO: 40) were designed and the reaction mixtures prepared by following the manufacturer's direction. The pBAD-PAL construct prepared above was used as template in the reaction below.

The 50 uL reaction mixture contained 1.0 uL of 50 ng/uL of template plasmid, 1.0 uL of 10 pmol/uL of each primer, 5 uL of 10× reaction buffer, 1.0 uL of dNTP mix and 3 uL of Quik solution, 30 uL of water and 1.0 uL of pfu-ultra high fidelity DNA polymerase in a thin wall 200 uL tube. All reagents and the polymerase used in this reaction were provided in the above QuikChange II XL kit. The reaction was carried out in a DNA Thermocycler GeneAmp 2400 (PE Applied Biosystems, Foster city, Calif.) using the following conditions. The starting temperature was 96° C. for 2 min, after which 18 heating/cooling cycles were performed. Each cycle consisted of 96° C. for 30 sec, followed by 60° C. for 30 sec, and 72° C. for 160 sec. At the completion of the temperature cycling, the samples were kept at 72° C. for 600 sec more, and then held awaiting sample recovery at 4° C.

Following completion of the reaction, 1.0 uL of the restriction enzyme DpnI (from the above kit) was added to the reaction, followed by incubation at 37° C. for 3 h to digest the template plasmids in the reaction.

2.0 uL of the DpnI digested reaction product was then transformed into 50 ul of E. coli TOP10 electro competent cells (Invitrogen) using a Bio RAD Gene Pulser II (Bio-Rad Laboratories Inc, Hercules, Calif.) by following the manufacturer's direction. Different volumes (2.0 uL, 5.0 uL and 20 uL) of the transformed cells were streaked on 10 cm agar plates containing the LB medium and 100 ug/mL of ampicillin, and the plates were incubated at 37° C. overnight. Three clones were picked from the plate containing well-separated colonies. The plasmids from the three clones were purified using a Qiaprep spin miniprep kit (Qiagen, Valencia Calif., catalogue #27106) by following the manufacturer's instructions. The positive clones were confirmed by restriction digestion analysis using restriction enzymes EcoRI and Hind III (Promega, Madison, Wis.) by placing 1.0 uL of 10× reaction buffer (Promega buffer), 1.0 uL of the purified plasmid and 1.0 uL of each restriction enzyme in 6.0 uL of deionized water. The reaction mixture was incubated at 37° C. for 60 min. The digested product of each clone was separated on a 0.8% agarose E gel (Invitrogen, catalogue #G5018-08). One 2.1 kbp and one 4.0 kbp DNA fragment were detected on the gel in samples with both EcoRI and HindIII restrictions sites in the construct. The EcoRI site in this construct was then replaced by SacI site using the same protocol described above with plasmid template pBAD-PAL-EcoRI and primers SEQ ID Nos: 13 and 14.

The positive clones were confirmed by restriction digestion analysis using restriction enzymes SacI and Hind III (Promega, Madison, Wis.). Once the positive clones were identified, the above restriction digestion reaction was set up in a larger scale (50 uL). The 4 kbp fragment containing the digested vector gel purified from the mix using a 1% agarose gel and QIAquick gel extraction kit (Qiagen, Valencia Calif., catalogue #28704) by following the manufacturer's protocol. This construct was named pBAD-SacI.

Host Strains Used for Over-Expressing KARI

The host strain E. coli Bw25113 (ΔilvC), an ilvC gene-knockout, was used for making constructs over-expressing the KARI enzyme. In this strain, the entire ilvC gene on the E. coli chromosome was replaced by a Kanamycin cassette using the Lambda red homology recombination technology (Datsenko and Wanner, Proc. Natl. Acad. Sci. USA. 97, 6640-6645, 2000). All of the strains and vectors needed for the creation of the knockout strain using this technology were obtained from Prof. Barry Wanner (Purdue University, West Lafayette, Ind.).

Preparation of the ilvC Coding Region for Cloning

The coding region for ilvC was amplified using high fidelity pfu-ultra polymerase (Stratagene, La Jolla, Calif.) with the addition of a SacI site to the 5' end of the forward primer right before the ATG and a HindIII site added to the 5' end of the reverse primer right after the stop codon. The primer with SEQ ID No: 15 (Forward: ilvc-trc-SacI-F) and primer with SEQ ID No: 16 (Reverse: ilvc-trc-HindIII-R) were used for this reaction. The template used in the PCR reaction was the ptrc99A-ilvC construct described above.

A 50 uL reaction mixture contained 5.0 uL of 10× reaction buffer supplied with the pfu-ultra polymerase (Stratagene), 1.0 uL of 50 ng/uL template, 1.0 uL each of 10 pmol/uL forward and reverse primers, 1.0 uL of 40 mM dNTP mix (Clonetech, Mountain View, Calif.), 1.0 uL pfu-ultra DNA polymerase (Stratagene) and 39 uL water. This reaction mixture was placed in a thin well 200 uL tube for the PCR reaction in a DNA Thermocycler GeneAmp 2400 (PE Applied Biosystems, Foster city, Calif.). The following conditions were used for performing the PCR reaction. The starting temperature was 94° C. for 2 min. Then 30 heating/cooling cycles were performed. Each cycle consisted of 94° C. for 30 sec, 58° C. for 30 sec, and 68° C. for 1 min and 40 sec. At the completion of the temperature cycling, the samples were kept at 60° C. for 10 min more, and then held awaiting sample recovery at 4° C.

The PCR product was partially purified using a QIAquik PCR purification kit (Qiagen, cat #28106) and digested by HindIII and SacI, then gel purified using the protocol as described above. The digested PCR fragment was ligated into the pBAD-SacI vector digested by the same set of enzymes.

The 20 uL ligation reaction contained 1.0 uL T4 DNA ligase (Promega) 2.0 uL of 10× reaction buffer that comes with the T4 DNA ligase, 45 ng of vector and 45 ng of insert and deionized water. The reaction was incubated at 16° C. overnight in an Eppendorf thermal cycler (Eppendorf North America, Westbury, N.Y.).

Two uL of the ligation product was transformed into E. coli TOP10 electro-competent cells (Invitrogen), using a Bio-RAD Gene Pulser II (Bio-Rad Laboratories Inc., Hercules, Calif.). The transformed clones were selected on agar plates containing the LB medium and 100 ug/mL ampicillin. The presence of the E. coli ilvC gene insert in the clone was confirmed by SacI digestion and DNA sequencing using primers SEQ ID Nos: 17-22. The construct with the ilvC gene insert was named pBAD-K12-ilvC Preparation of Strains for Analysis of KARI Expression Plasmids of the above pBAD-K12-ilvC construct and pTrc99A-ilvC, both in TOP10 host strain, were prepared from 3 mL of overnight culture in the LB medium containing 100 ug/mL ampicillin using Qiaprep spin miniprep kit (Qiagen, Valencia Calif., catalogue #27106) following manufacturer's instructions. One uL of pBAD-K12-ilvC and one uL of pTrc99A-ilvC were transformed separately to E. coli Bw25113 (ΔilvC) electro-competent cells using a Bio RAD Gene Pulser II (Bio-Rad Laboratories Inc, Hercules, Calif.) by following the manufacturer's directions. The transformed cells were streaked onto agar plates containing the LB medium plus 100 ug/mL ampicillin and incubated overnight at 37° C. Colonies from these plates were used for preparation of cell free extracts.

Preparation of Cell Free Extract

Cells containing pBAD-K12-ilvC and pTrc99A-ilvC were grown in 3.0 mL of the LB medium containing 100 ug/mL ampicillin and inducer 0.02% (w/v) arabinose and 1 mM Isopropyl β-D-1-thiogalactopyranoside (IPTG) respectively, at 37° C. while shaking at 250 rpm. The cells were harvested by centrifugation at 6000×g for 5 min at 22.5° C., cell pellets were resuspended in 300 uL of 100 mM HEPES buffer (pH7.5) in a 1.5 mL micro-centrifuge tube, placed in a water bath filled with 40% water and 60% ice (by volume), and sonicated for 2-3 min (3.0 sec bursts at 1.0 force followed by 3.0 sec rest) using a Misonix 300 sonicator (Misonix, Farmingdale N.Y.). The cell debris was removed by centrifugation (Eppendorf micro-centrifuge, model 5415D, at 9300×g for 5 min at 22.5° C.).

Alternatively cell extracts were prepared using the detergent based protein extraction reagent BugBuster master mix (Novagen, catalogue#71456). The cell pellets from 3.0 mL of cultures were resuspended in 300 uL of BugBuster master mix and incubated at room temperature for 20 min. The cell debris was removed by centrifugation (Eppendorff micro-centrifuge model 5415D) at 9300×g at 22.5° C. for 5 min.

Protein Quantification

The total protein concentration in samples was measured by the Bradford Coomassie Assay (BCA) using Coomassie Plus (Pierce #23238, Rockford, Ill.). The samples and protein standards (Bovine Serum Albumin, BSA) were set up in a 96-well microplate following the manufacturer's protocol. The concentration of protein was measured following absorbance at 595 nm using a SpectraMax plate reader (Molecular Devices Corporation, Sunnyvale, Calif.).

KARI Enzyme Assay Protocol

The assay substrate, (R,S)-acetolactate, was synthesized as described by Aulabaugh and Schloss (Aulabaugh and Schloss, *Biochemistry*, 29, 2824-2830, 1990): 1.0 g of 2-acetoxy-2-methyl-3-oxobutyric acid ethyl ester (Aldrich, Milwaukee, Wis.) was mixed with 10 mL 1.0 M NaOH and stirred at room temperature. When the solution pH became neutral, additional NaOH was slowly added to maintain the pH ~8.0. All other chemicals used in the assay were purchased from Sigma.

The enzymatic conversion of acetolactate to 2,3-dihydroxyisovalerate by KARI was followed by measuring the disappearance of the cofactor, NADPH, from the reaction at 340 nm using a spectrophotometer (Agilent Technologies, Santa Clara, Calif.). The activity was calculated using the molar extinction coefficient of 6220 $M^{-1}cm^{-1}$ for NADPH. The stock solutions used were: 100 mM HEPES-potassium salt, adjusted by HCl/KOH to pH 7.5; 1.0 M $MgCl_2$; 20 mM NADPH and 90 mM acetolactate. The 40 mL reaction buffer mix stock containing 100 mM HEPES stock and 400 uL $MgCl_2$ stock.

The reaction buffer (194 uL) was mixed with NADPH (2.0 uL) stock and cell extract (2.0 uL) in a plastic disposable cuvette (Eppendorf UVette, Eppendorf AG, Hamburg, Germany) and the absorbance at 340 nm at 22.5° C. was recorded for 20 seconds. Initial $A_{340}$ was usually ~0.9-1.0. Then acetolactate (2.0 uL) was added to the cuvette to start the reaction. The final concentration of ingredients in the assay was: 100 mM potassium HEPES at pH7.5, 10 mM $MgCl_2$, 200 uM NADPH and 900 uM acetolactate. This solution was mixed thoroughly and its absorbance at 340 nm for additional 80 sec was recorded. The KARI activity reported here is defined as μmole of NADPH consumed per min per mg of total protein in cell extracts. The results of protein concentrations and KARI activities in cell extracts prepared from E. coli Bw25113 (ΔilvC) cells transformed with pBAD-K12-ilvC plasmids and ptrc99A-ilvC plasmids are shown in Table 4. Two cell extract samples were prepared for the pBAD-K12-ilvC construct, one by sonication the other using the BugBuster. The cell extract sample for pTrc99A-ilvC construct was prepared by using the BugBuster. These analyses showed that the KARI protein was expressed at a higher level in the cells containing pBAD-K12-ilvC plasmids than those containing pTrc99A-ilvC, however, enzyme specific activities in the cell extract samples prepared by two different methods were not significantly different. E. coli strain Bw25113 transformed with pBAD-HisB (Invitrogen) was used as the negative control. The rate of NADPH consumption in the negative control was extremely low (about 1% to 2% of the consumption rate measured for those containing the pBAD-K12-ilvC gene).

TABLE 4

KARI and Total Protein Concentration in Clones CONTAINING ilvC GENE

| Clones | total protein (μg/ml) | KARI Activity umole/min/mg total protein |
|---|---|---|
| BW25113(ΔilvC)-ptrc99A-ilvC-Bugbuster | 8007 | 0.16 |
| BW25113(ΔilvC)-pBAD-K12-ilvC-sonication | 9707 | 0.83 |
| BW25113(ΔilvC)-pBAD-K12-ilvC-BugBuster | 4595 | 0.78 |

Example 2

Identification of KARI with High Specific Activity Enzyme from Various Microorganisms The purpose of this Example is to describe how to identify microorganisms that contain KARI enzymes with high specific activity.

It was hypothesized that those KARI-containing organisms with faster doubling times than *E. coli*, during growth in a minimal medium, will contain highly active KARI enzymes. Three microorganisms, *Pseudomonas aeruginosa* (PAO1), *Pseudomonas fluorescens* (PF5), and *Vibrio cholerae* (N16961), were identified with faster doubling times than *E. coli* when grown in the M9 minimal medium (See below). Genomic DNA preparations of these organisms are commercially available. Table 5 shows the doubling times of these organisms compared to *E. coli* following growth in the minimal M9 medium.

TABLE 5

DOUBLING TIMES OF STRAINS TESTED DURING GROWTH IN THE M9 MEDIUM

| Organism | Doubling time in M9 medium | Reference |
| --- | --- | --- |
| E. coli | 55-60 min | 1 |
| V. cholerae (N16961) | 45 min | 3 |
| P. aeruginosa (PAO1) | 42 min | 2 |
| P. fluorescens (PF5) | 38 min | 2 |

REFERENCES
1. Neidhardt, F C, et al. J, Bacteriol. 119, 736-747, 1974.
2. Brinkman F S L, et al. J. Bacteriol. 181, 4746-4754, 1999.
3. Silva A J and Benitez J A, J. Bacteriol. 188, 794-800, 2006.

As stated above, KARI enzymes have been grouped in different classes. The *Pseudomonas* PF5 and PAO1 enzymes belong to the class I KARI group, which is the largest group in the family, while the *E. coli* and *V. Cholerae* enzymes belong to the class II bacterial KARI group.

The purified genomic DNAs of *P. aeruginosa* (PAO1, ATCC 47085), and *P. fluorescens* (PF5, ATCC BAA-477) were purchased from ATCC (American Type Culture Collection, 10801 University Blvd, Manassas, Va.). The genomic DNA from each organism (10 ug each) was rehydrated in 100 uL of 10 mM Tris-HCl, pH 8.5 for use in a PCR reaction. The following pairs of primers, with SacI site attached to the forward primers (SEQ ID Nos: 23 and 25) and HindIII site attached to the reverse primers (SEQ ID Nos: 24 and 26) were used to amplify the ilvC gene coding regions from the genomic DNAs of PAO1 and PF5 by PCR using high fidelity pfu-ultra DNA polymerase (Stratagene). The primers were designed based the publically available (GeneBank) sequences of PF5 and PAO1 ilvC genes for these organisms.

Each 50 uL PCR reaction contained 1.0 uL of genomic DNA and 1.0 uL each of 10 pmol/uL of forward and reverse primers for the respective genes.

The PCR reactions were carried out in an Eppendorf master cyclers gradient (Eppendorf North America, Westbury, N.Y.) using the following reaction conditions. The starting temperature was 95° C. for 2 min. Then 5 heating/cooling cycles were performed. Each cycle consisted of 95° C. for 30 sec, 55° C. for 30 sec, and 72° C. for 1 min and 30 sec. Then 25 further heating/cooling cycles were performed. Each of these cycles consisted of 95° C. for 30 sec, 65° C. for 30 sec, and 72° C. for 1.0 min and 30 sec. At the completion of these temperature cycles, the samples were kept at 72° C. for 10 min more, and then held awaiting sample recovery at 4° C.

The resulting PCR fragments were digested by HindIII and SacI, cloned into the pBAD-SacI expression vector, and transformed into the ilvC-knockout strain BW25113(ΔilvC) using procedures described in Example I. Positive clones were identified by restriction enzyme digestion and validated by full length DNA sequencing using primers, SEQ ID No: 21 (pBAD-eF1), SEQ ID No: 22 (PALPK-R1), SEQ ID No: 27 (PF5-S-F2), and SEQ ID No: 28 (PF5-S-R2): The resulting strains were named BW25113(ΔilvC)-PAO1-ilvC and BW25113(ΔilvC)-PF5-ilvC.

The *V. cholerae* VC0162 gene coding region was codon optimized for *E. coli* expression, based on the known protein sequence (Accession NP_229819.1) and prepared by synthetic custom gene synthesis (DNA 2.0, Inc. Menlo Park, Calif.). It was prepared with SacI and HindIII sites attached to the ends of the gene. This DNA fragment was also cloned into the pBAD-SacI expression vector using SacI and HindIII restriction sites and transformed into the ilvC-knockout strain BW25113(ΔilvC). The resulting strain was named BW25113(ΔilvC)-VCopt-VC0162. The sequence of the codon-optimized VC0162 is given as SEQ ID No: 30.

Protein and KARI activity assays from K12, PAO1, PF5 and VC strains

Cell free extracts of strains BW25113(ΔilvC)-K12-ilvC, BW25113(ΔilvC)-PAO1-ilvC. BW25113(ΔilvC)-PF5-ilvC and BW25113(ΔilvC)-VCopt-VC0162 all expressing the KARI enzyme were prepared using BugBuster as described in Example 1. The KARI assay was performed using 188 uL of the reaction buffer, 2.0 uL of 20 mM NADPH stock, 5.0 uL of 20% cell extract diluted in assay buffer and 5.0 uL of 90 mM actolactate. The final assay solution used in this example therefore consisted of enzyme, 100 mM potassium-HEPES, 10 mM $MgCl_2$, 200 uM NADPH and 2.25 mM acetolactate.

Table 6 shows KARI specific activities of four different organisms grown overnight in the presence of 0.02% (w/v) of arabinose as the inducer. The amount of total protein in the cell extract and the KARI activity were measured as described above. As outlined in Table 6, the KARI enzymes from the organisms identified with faster doubling times when grown in a minimal medium (Table 5) all have higher specific activity than the KARI from *E. coli*. Each of the extracts had approximately equal levels of expression of the KARI protein as estimated by SDS-PAGE (data not shown). These results support the hypothesis that the doubling time during growth in minimal media can be used as a means to identify KARI enzymes with higher specific activity.

TABLE 6

COMPARISON OF KARI SPECIFIC ACTIVITIES FROM DIFFERENT ORGANISMS

| strain | MW (KDa) | KARI class | total protein in cell extract ug/ml | KARI specific activity umol/min/mg total protein |
| --- | --- | --- | --- | --- |
| BW25113(ΔilvC)-K12-ilvC | 54 | II | 6693 | 0.72 |
| BW25113(ΔilvC)-VC-opt-VC0162 | 54 | II | 6730 | 1.1 |
| BW25113(ΔilvC)-PAO1-ilvC | 36 | I | 4988 | 1.2 |
| BW25113(ΔilvC)-PF5-ilvC | 36 | I | 7671 | 1.8 |

Example 3

Analysis of Specific Activity of Purified K12-KARI and the PF5-KARI

To better resolve increases in KARI specific activity observed with crude cell extracts in Example 2, K12-KARI and PF5-KARI were purified to homogeneity to allow accurate quantification of the concentration of individual proteins and determine specific activity of the purified KARI enzymes.

Purification of K12-KARI and PF5-KARI

Both K12-KARI and PF5-KARI were purified using the weak anion-exchange spin column, Vivapure IEX D, miniH (Vivascience AG, Hannover, Germany), followed by concentration in a Microcon device with 100 KDa molecular weight cutoff (YM100, Millpore, Bedford, Mass.). The purification procedure was carried out at room temperature (22.5° C.).

Stock solutions used in the anion-exchange spin column were: 100 mM potassium-HEPES at pH 7.0, 1.0 M $MgCl_2$, 250 mM EDTA, 10% Brij35 and 2 M KCl. Wash buffer (BufferA) was made by adding 5.0 mL of 100 mM HEPES stock to 15 mL water with the addition of 50 uL $MgCl_2$ stock, 20 uL EDTA stock and 10 uL of 10% Brij35. The elution buffer #1 (Buffer B) was made by adding 5.0 ml of 100 mM HEPES, 2.0 mL of KCl stock to 13 mL water with the addition of 50 ul MgCl2 stock, 20 uL EDTA stock and 10 uL of 10% Brij35. Elution buffer #2 (Buffer C) was made by adding 5 mL of 100 mM HEPES stock, 5.0 mL of KCl stock to 10 mL water with the addition of 50 uL $MgCl_2$ stock, 20 uL EDTA stock and 10 uL of 10% Brij35. The final KCl concentration in Buffer B is about 200 mM and about 500 mM in Buffer C.

Cell free extracts of strains BW25113(ΔilvC)-K12-ilvC and BW25113(ΔilvC)-PF5-ilvC were prepared using Bug-Buster as described in Example 1. To prepare the dilute cell extract for loading into the Vivapure IEX D columns, 600 uL of double deionized water was added to 200 uL of the extract.

Vivapure IEX D columns were first washed with 400 uL of buffer A by centrifugation (Eppendorf micro-centrifuge model 5415D) at 2000×g for 5 min. An identical equipment and process was used in the entire Vivapure IEX D purification procedure. The dilute cell extract (described above) was loaded onto the column and centrifuged in two batches of 400 uL each. The column was then washed (×2) with 400 uL of buffer A. For PF5-KARI sample, 400 uL of buffer B was loaded to elute the enzyme from the column into a collection tube. For K12-KARI sample, 400 uL of buffer C was used instead.

Microcon YM100 devices were first washed with 400 uL of deionized water by centrifugation (Eppendorf micro-centrifuge model 5415D) at 13800×g for 5 min. The sample collected from the Vivapure IEX D purification was then loaded and centrifuged at 13800×g for 4 min. The flow-though was discarded and 400 uL of buffer B was added to the sample chamber and centrifuged at 13800×g for 4 min. The wash procedure was repeated (×2) before 200 uL of buffer B was added to the sample chamber. The sample chamber was inverted to a clean collection tube and centrifuged at 5000×g for 2 min to collect the purified sample.

The purity of each purified KARI sample was validated by capillary-electrophoresis (Agilent 2100 Bioanalyzer, Agilent Technology, Santa Clara, Calif.). Samples were prepared using the Protein 230 reagent kit and applied to a Protein Labchip (supplied with the reagent kits) following the manufacturer's instruction and analyzed by the Bioanalyzer. A single peak with little background was observed on the electrogram for each purified sample.

Protein Quantification of Purified KARI Samples

The UV absorption measurement of the purified KARI samples at 280 nm was performed using a spectrophotometer (Agilent Technology, Santa Clara, Calif.) and 1 cm path length disposable plastic cuvettes (UVette, eppendorf, Hamburg, Germany) to quantify the amount of KARI in the purified samples. The extinction coefficients at 280 nm for PF5-KARI (0.73 for 1 mg/mL), and K12-KARI (0.98 for 1 mg/mL) were predicted by the program Protparam available on ExPASy web site (Pace, C. N., et al., Protein Sci. 11, 2411-2423, 1995). The purified sample was diluted to 20% (v/v) in buffer B for the UV absorption measurement. The $A_{280}$ for the diluted PF5-KARI sample was 0.41 and for the diluted K12-KARI was 0.36.

Activity Assay for Purified KARI

The assay condition used in this example was the same as in Example 2, except that 5 uL of 20% (v/v) purified sample was used instead of cell extract. The protein concentrations of the purified samples and their specific activities are shown in Table 7. The specific activity of purified PF5-KARI, the fastest grower tested, was twice the specific activity of K12-KARI. These results are consistent with the data obtained using crude preparations of these two enzymes in Example 2 thus providing further support for the hypothesis that the doubling time during growth in minimal media can be used as a means to identify KARI enzymes with higher specific activity compared to the *E. coli* enzyme.

TABLE 7

CONCENTRATION AND SPECIFIC ACTIVITY OF KARI IN *E. COLI* AND *PSEUDOMONAS* STRAINS

| Sample | KARI concentration (mg/ml) | Specific activity umol/min/mg KARI |
|---|---|---|
| K12-KARI | 1.85 | 1.1 |
| PF5-KARI | 2.80 | 2.2 |

What is claimed is:

1. A method for the production of isobutanol comprising:
   (a) providing a recombinant yeast host cell comprising an isobutanol producing biosynthetic pathway comprising at least one genetic construct encoding a polypeptide having ketol-acid reductoisomerase activity, wherein the polypeptide having ketol-acid reductoisomerase activity comprises an amino acid sequence of SEQ ID NO: 34, SEQ ID NO: 35, or SEQ ID NO: 36 and a specific activity of greater than 1.1 µmoles/min/mg for the conversion of (S)-acetolactate to 2,3-dihydroxyisovalerate;
   (b) growing the yeast host cell of (a) under conditions where isobutanol is produced;
   wherein the ketol-acid reductoisomerase specific activity greater than 1.1 µmoles/min/mg is based on purified protein as measured by:

A) NADPH consumption assay, run under the following conditions:
   i) pH of about 7.5,
   ii) a temperature of about 22.5° C., and
   iii) a reaction buffer comprising:
      a) 100 mM potassium-HEPES,
      b) 10 mM $MgCl_2$,
      c) 2.25 mM (R,S)-acetolactate, and
      d) 200 µM NADPH; and
B) purified protein concentration as determined by absorbance at 280 nanometers.

2. The method according to claim 1 wherein the host cell is a member of a genus selected from the group consisting of *Pichia, Candida, Hansenula*, and *Saccharomyces*.

3. The method according to claim 2 wherein the cell is *Saccharomyces cerevisiae*.

4. The method according to claim 1, wherein the polypeptide having ketol-acid reductoisomerase activity comprises the amino acid sequence of SEQ ID NO:36.

5. The method according to claim 1, wherein the polypeptide having ketol-acid reductoisomerase activity comprises the amino acid sequence of SEQ ID NO:35.

* * * * *

SEQUENCE LISTING

```
<160> NUMBER OF SEQ ID NOS: 40

<210> SEQ ID NO 1
<211> LENGTH: 1680
<212> TYPE: DNA
<213> ORGANISM: K. pneumoniae

<400> SEQUENCE: 1
atggacaaac agtatccggt acgccagtgg gcgcacggcg ccgatctcgt cgtcagtcag      60
```

-continued

| | |
|---|---|
| ctggaagctc agggagtacg ccaggtgttc ggcatccccg gcgccaaaat cgacaaggtc | 120 |
| tttgattcac tgctggattc ctccattcgc attattccgg tacgccacga agccaacgcc | 180 |
| gcatttatgg ccgccgccgt cggacgcatt accggcaaag cgggcgtggc gctggtcacc | 240 |
| tccggtccgg gctgttccaa cctgatcacc ggcatggcca ccgcgaacag cgaaggcgac | 300 |
| ccggtggtgg ccctgggcgg cgcggtaaaa cgcgccgata agcgaagca ggtccaccag | 360 |
| agtatggata cggtggcgat gttcagcccg gtcaccaaat acgccatcga ggtgacggcg | 420 |
| ccggatgcgc tggcggaagt ggtctccaac gccttccgcg ccgccgagca gggccggccg | 480 |
| ggcagcgcgt tcgttagcct gccgcaggat gtggtcgatg gcccggtcag cggcaaagtg | 540 |
| ctgccggcca gcggggcccc gcagatgggc gccgcgccgg atgatgccat cgaccaggtg | 600 |
| gcgaagctta tcgcccaggc gaagaacccg atcttcctgc tcggcctgat ggccagccag | 660 |
| ccggaaaaca gcaaggcgct gcgccgtttg ctggagacca gccatattcc agtcaccagc | 720 |
| acctatcagg ccgccggagc ggtgaatcag gataacttct ctcgcttcgc cggccgggtt | 780 |
| gggctgtttta caaccaggc cggggaccgt ctgctgcagc tcgccgacct ggtgatctgc | 840 |
| atcggctaca gcccggtgga atacgaaccg gcgatgtgga acagcggcaa cgcgacgctg | 900 |
| gtgcacatcg acgtgctgcc cgcctatgaa gagcgcaact acaccccgga tgtcgagctg | 960 |
| gtgggcgata tcgccggcac tctcaacaag ctggcgcaaa atatcgatca tcggctggtg | 1020 |
| ctctccccgc aggcggcgga gatcctccgc gaccgccagc accagcgcga gctgctggac | 1080 |
| cgccgcggcg cgcagctcaa ccagtttgcc ctgcatcccc tgcgcatcgt tcgcgccatg | 1140 |
| caggatatcg tcaacagcga cgtcacgttg accgtggaca tgggcagctt ccatatctgg | 1200 |
| attgcccgct acctgtacac gttccgcgcc cgtcaggtga tgatctccaa cggccagcag | 1260 |
| accatgggcg tcgccctgcc ctgggctatc ggcgcctggc tggtcaatcc tgagcgcaaa | 1320 |
| gtggtctccg tctccggcga cggcggcttc ctgcagtcga gcatggagct ggagaccgcc | 1380 |
| gtccgcctga agccaacgt gctgcatctt atctgggtcg ataacggcta caacatggtc | 1440 |
| gctatccagg aagagaaaaa atatcagcgc ctgtccggcg tcgagtttgg gccgatggat | 1500 |
| tttaaagcct atgccgaatc cttcggcgcg aaagggtttg ccgtggaaag cgccgaggcg | 1560 |
| ctggagccga ccctgcgcgc ggcgatggac gtcgacggcc cggcggtagt ggccatcccg | 1620 |
| gtggattatc gcgataaccc gctgctgatg ggccagctgc atctgagtca gattctgtaa | 1680 |

<210> SEQ ID NO 2
<211> LENGTH: 559
<212> TYPE: PRT
<213> ORGANISM: K. pneumoniae

<400> SEQUENCE: 2

```
Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
                20                  25                  30

Pro Gly Ala Lys Ile Asp Lys Val Phe Asp Ser Leu Leu Asp Ser Ser
            35                  40                  45

Ile Arg Ile Ile Pro Val Arg His Glu Ala Asn Ala Ala Phe Met Ala
        50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95
```

```
Ser Glu Gly Asp Pro Val Val Ala Leu Gly Ala Val Lys Arg Ala
            100                 105                 110

Asp Lys Ala Lys Gln Val His Gln Ser Met Asp Thr Val Ala Met Phe
            115                 120                 125

Ser Pro Val Thr Lys Tyr Ala Ile Glu Val Thr Ala Pro Asp Ala Leu
            130                 135                 140

Ala Glu Val Val Ser Asn Ala Phe Arg Ala Glu Gln Gly Arg Pro
145                 150                 155                 160

Gly Ser Ala Phe Val Ser Leu Pro Gln Asp Val Val Asp Gly Pro Val
                165                 170                 175

Ser Gly Lys Val Leu Pro Ala Ser Gly Ala Pro Gln Met Gly Ala Ala
            180                 185                 190

Pro Asp Asp Ala Ile Asp Gln Val Ala Lys Leu Ile Ala Gln Ala Lys
            195                 200                 205

Asn Pro Ile Phe Leu Leu Gly Leu Met Ala Ser Gln Pro Glu Asn Ser
            210                 215                 220

Lys Ala Leu Arg Arg Leu Leu Glu Thr Ser His Ile Pro Val Thr Ser
225                 230                 235                 240

Thr Tyr Gln Ala Ala Gly Ala Val Asn Gln Asp Asn Phe Ser Arg Phe
                245                 250                 255

Ala Gly Arg Val Gly Leu Phe Asn Asn Gln Ala Gly Asp Arg Leu Leu
            260                 265                 270

Gln Leu Ala Asp Leu Val Ile Cys Ile Gly Tyr Ser Pro Val Glu Tyr
            275                 280                 285

Glu Pro Ala Met Trp Asn Ser Gly Asn Ala Thr Leu Val His Ile Asp
            290                 295                 300

Val Leu Pro Ala Tyr Glu Glu Arg Asn Tyr Thr Pro Asp Val Glu Leu
305                 310                 315                 320

Val Gly Asp Ile Ala Gly Thr Leu Asn Lys Leu Ala Gln Asn Ile Asp
                325                 330                 335

His Arg Leu Val Leu Ser Pro Gln Ala Ala Glu Ile Leu Arg Asp Arg
            340                 345                 350

Gln His Gln Arg Glu Leu Leu Asp Arg Arg Gly Ala Gln Leu Asn Gln
            355                 360                 365

Phe Ala Leu His Pro Leu Arg Ile Val Arg Ala Met Gln Asp Ile Val
            370                 375                 380

Asn Ser Asp Val Thr Leu Thr Val Asp Met Gly Ser Phe His Ile Trp
385                 390                 395                 400

Ile Ala Arg Tyr Leu Tyr Thr Phe Arg Ala Arg Gln Val Met Ile Ser
                405                 410                 415

Asn Gly Gln Gln Thr Met Gly Val Ala Leu Pro Trp Ala Ile Gly Ala
            420                 425                 430

Trp Leu Val Asn Pro Glu Arg Lys Val Val Ser Val Ser Gly Asp Gly
            435                 440                 445

Gly Phe Leu Gln Ser Ser Met Glu Leu Glu Thr Ala Val Arg Leu Lys
            450                 455                 460

Ala Asn Val Leu His Leu Ile Trp Val Asp Asn Gly Tyr Asn Met Val
465                 470                 475                 480

Ala Ile Gln Glu Glu Lys Lys Tyr Gln Arg Leu Ser Gly Val Glu Phe
                485                 490                 495

Gly Pro Met Asp Phe Lys Ala Tyr Ala Glu Ser Phe Gly Ala Lys Gly
            500                 505                 510
```

```
Phe Ala Val Glu Ser Ala Glu Ala Leu Glu Pro Thr Leu Arg Ala Ala
        515                 520                 525

Met Asp Val Asp Gly Pro Ala Val Val Ala Ile Pro Val Asp Tyr Arg
        530                 535                 540

Asp Asn Pro Leu Leu Met Gly Gln Leu His Leu Ser Gln Ile Leu
545                 550                 555

<210> SEQ ID NO 3
<211> LENGTH: 1476
<212> TYPE: DNA
<213> ORGANISM: E. coli

<400> SEQUENCE: 3
atggctaact acttcaatac actgaatctg cgccagcagc tggcacagct gggcaaatgt      60
cgctttatgg gccgcgatga attcgccgat ggcgcgagct accttcaggg taaaaaagta     120
gtcatcgtcg gctgtggcgc acagggtctg aaccagggcc tgaacatgcg tgattctggt     180
ctcgatatct cctacgctct gcgtaaagaa gcgattgccg agaagcgcgc gtcctggcgt     240
aaagcgaccg aaaatggttt taaagtgggt acttacgaag aactgatccc acaggcggat     300
ctggtgatta acctgacgcc ggacaagcag cactctgatg tagtgcgcac cgtacagcca     360
ctgatgaaag acggcgcggc gctgggctac tcgcacggtt tcaacatcgt cgaagtgggc     420
gagcagatcc gtaaagatat caccgtagtg atggttgcgc cgaaatgccc aggcaccgaa     480
gtgcgtgaag agtacaaacg tgggttcggc gtaccgacgc tgattgccgt tcacccggaa     540
aacgatccga aggcgaagg catggcgatt gccaaagcct gggcggctgc aaccggtggt     600
caccgtgcgg gtgtgctgga atcgtccttc gttgcggaag tgaaatctga cctgatgggc     660
gagcaaacca tcctgtgcgg tatgttgcag gctggctctc tgctgtgctt cgacaagctg     720
gtggaagaag taccgatcc agcatacgca gaaaaactga ttcagttcgg ttgggaaacc     780
atcaccgaag cactgaaaca gggcggcatc accctgatga tggaccgtct ctctaacccg     840
gcgaaactgc gtgcttatgc gctttctgaa cagctgaaag atcatggc accccctgttc     900
cagaaacata tggacgacat catctccggc gaattctctt ccggtatgat ggcggactgg     960
gccaacgatg ataagaaact gctgacctgg cgtgaagaga ccggcaaaac cgcgtttgaa    1020
accgcgccgc agtatgaagg caaaatcggc gagcaggagt acttcgataa aggcgtactg    1080
atgattgcga tggtgaaagc gggcgttgaa ctggcgttcg aaaccatggt cgattccggc    1140
atcattgaag agtctgcata ttatgaatca ctgcacgagc tgccgctgat tgccaacacc    1200
atcgcccgta agcgtctgta cgaaatgaac gtggttatct ctgataccgc tgagtacggt    1260
aactatctgt ctcttacgc ttgtgtgccg ttgctgaaac cgtttatggc agagctgcaa    1320
ccgggcgacc tgggtaaagc tattccggaa ggcgcggtag ataacgggca actgcgtgat    1380
gtgaacgaag cgattcgcag ccatgcgatt gagcaggtag gtaagaaact gcgcggctat    1440
atgacagata tgaaacgtat tgctgttgcg ggttaa                              1476

<210> SEQ ID NO 4
<211> LENGTH: 491
<212> TYPE: PRT
<213> ORGANISM: E. coli

<400> SEQUENCE: 4

Met Ala Asn Tyr Phe Asn Thr Leu Asn Leu Arg Gln Gln Leu Ala Gln
1               5                  10                  15

Leu Gly Lys Cys Arg Phe Met Gly Arg Asp Glu Phe Ala Asp Gly Ala
```

```
            20                  25                  30
Ser Tyr Leu Gln Gly Lys Lys Val Val Ile Val Gly Cys Gly Ala Gln
         35                  40                  45
Gly Leu Asn Gln Gly Leu Asn Met Arg Asp Ser Gly Leu Asp Ile Ser
         50                  55                  60
Tyr Ala Leu Arg Lys Glu Ala Ile Ala Glu Lys Arg Ala Ser Trp Arg
 65                  70                  75                  80
Lys Ala Thr Glu Asn Gly Phe Lys Val Gly Thr Tyr Glu Glu Leu Ile
                 85                  90                  95
Pro Gln Ala Asp Leu Val Ile Asn Leu Thr Pro Asp Lys Gln His Ser
                100                 105                 110
Asp Val Val Arg Thr Val Gln Pro Leu Met Lys Asp Gly Ala Ala Leu
                115                 120                 125
Gly Tyr Ser His Gly Phe Asn Ile Val Glu Val Gly Glu Gln Ile Arg
                130                 135                 140
Lys Asp Ile Thr Val Val Met Val Ala Pro Lys Cys Pro Gly Thr Glu
145                 150                 155                 160
Val Arg Glu Glu Tyr Lys Arg Gly Phe Gly Val Pro Thr Leu Ile Ala
                165                 170                 175
Val His Pro Glu Asn Asp Pro Lys Gly Glu Gly Met Ala Ile Ala Lys
                180                 185                 190
Ala Trp Ala Ala Ala Thr Gly Gly His Arg Ala Gly Val Leu Glu Ser
                195                 200                 205
Ser Phe Val Ala Glu Val Lys Ser Asp Leu Met Gly Glu Gln Thr Ile
                210                 215                 220
Leu Cys Gly Met Leu Gln Ala Gly Ser Leu Leu Cys Phe Asp Lys Leu
225                 230                 235                 240
Val Glu Glu Gly Thr Asp Pro Ala Tyr Ala Glu Lys Leu Ile Gln Phe
                245                 250                 255
Gly Trp Glu Thr Ile Thr Glu Ala Leu Lys Gln Gly Gly Ile Thr Leu
                260                 265                 270
Met Met Asp Arg Leu Ser Asn Pro Ala Lys Leu Arg Ala Tyr Ala Leu
                275                 280                 285
Ser Glu Gln Leu Lys Glu Ile Met Ala Pro Leu Phe Gln Lys His Met
                290                 295                 300
Asp Asp Ile Ile Ser Gly Glu Phe Ser Ser Gly Met Met Ala Asp Trp
305                 310                 315                 320
Ala Asn Asp Asp Lys Lys Leu Leu Thr Trp Arg Glu Glu Thr Gly Lys
                325                 330                 335
Thr Ala Phe Glu Thr Ala Pro Gln Tyr Glu Gly Lys Ile Gly Glu Gln
                340                 345                 350
Glu Tyr Phe Asp Lys Gly Val Leu Met Ile Ala Met Val Lys Ala Gly
                355                 360                 365
Val Glu Leu Ala Phe Glu Thr Met Val Asp Ser Gly Ile Ile Glu Glu
                370                 375                 380
Ser Ala Tyr Tyr Glu Ser Leu His Glu Leu Pro Leu Ile Ala Asn Thr
385                 390                 395                 400
Ile Ala Arg Lys Arg Leu Tyr Glu Met Asn Val Val Ile Ser Asp Thr
                405                 410                 415
Ala Glu Tyr Gly Asn Tyr Leu Phe Ser Tyr Ala Cys Val Pro Leu Leu
                420                 425                 430
Lys Pro Phe Met Ala Glu Leu Gln Pro Gly Asp Leu Gly Lys Ala Ile
                435                 440                 445
```

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490

<210> SEQ ID NO 5
<211> LENGTH: 1851
<212> TYPE: DNA
<213> ORGANISM: E. coli

<400> SEQUENCE: 5

| | | | | | |
|---|---|---|---|---|---|
| atgcctaagt | accgttccgc | caccaccact | catggtcgta | atatggcggg | tgctcgtgcg | 60 |
| ctgtggcgcg | ccaccggaat | gaccgacgcc | gatttcggta | agccgattat | cgcggttgtg | 120 |
| aactcgttca | cccaatttgt | accgggtcac | gtccatctgc | gcgatctcgg | taaactggtc | 180 |
| gccgaacaaa | ttgaagcggc | tggcggcgtt | gccaaagagt | tcaacaccat | tgcggtggat | 240 |
| gatgggattg | ccatgggcca | cggggggatg | ctttattcac | tgccatctcg | cgaactgatc | 300 |
| gctgattccg | ttgagtatat | ggtcaacgcc | cactgcgccg | acgccatggt | ctgcatctct | 360 |
| aactgcgaca | aaatcacccc | gggggatgctg | atggcttccc | tgcgcctgaa | tattccggtg | 420 |
| atctttgttt | ccggcggccc | cgatggaggcc | gggaaaacca | aacttccga | tcagatcatc | 480 |
| aagctcgatc | tggttgatgc | gatgatccag | ggcgcagacc | cgaaagtatc | tgactcccag | 540 |
| agcgatcagg | ttgaacgttc | cgcgtgtccg | acctgcggtt | cctgctccgg | gatgtttacc | 600 |
| gctaactcaa | tgaactgcct | gaccgaagcg | ctgggcctgt | cgcagccggg | caacggctcg | 660 |
| ctgctggcaa | cccacgccga | ccgtaagcag | ctgttcctta | tgctggtaa | acgcattgtt | 720 |
| gaattgacca | aacgttatta | cgagcaaaac | gacgaaagtg | cactgccgcg | taatatcgcc | 780 |
| agtaaggcg | cgtttgaaaa | cgccatgacg | ctggatatcg | cgatgggtgg | atcgactaac | 840 |
| accgtacttc | acctgctggc | ggcggcgcag | gaagcggaaa | tcgacttcac | catgagtgat | 900 |
| atcgataagc | tttcccgcaa | ggttccacag | ctgtgtaaag | ttgcgccgag | cacccagaaa | 960 |
| taccatatgg | aagatgttca | ccgtgctggt | ggtgttatcg | gtattctcgg | cgaactggat | 1020 |
| cgcgcggggt | tactgaaccg | tgatgtgaaa | aacgtacttg | gcctgacgtt | gccgcaaacg | 1080 |
| ctggaacaat | acgacgttat | gctgacccag | gatgacgcgg | taaaaaatat | gttccgcgca | 1140 |
| ggtcctgcag | gcattcgtac | cacacaggca | ttctcgcaag | attgccgttg | ggatacgctg | 1200 |
| gacgacgatc | gcgccaatgg | ctgtatccgc | tcgctggaac | acgcctacag | caaagacggc | 1260 |
| ggcctggcgg | tgctctacgg | taactttgcg | gaaaacggct | gcatcgtgaa | acggcaggc | 1320 |
| gtcgatgaca | gcatcctcaa | attcaccggc | ccggcgaaag | tgtacgaaag | ccaggacgat | 1380 |
| gcggtagaag | cgattctcgg | cggtaaagtt | gtcgccggag | atgtggtagt | aattcgctat | 1440 |
| gaaggcccga | aggcggtcc | ggggatgcag | gaaatgctct | acccaaccag | cttcctgaaa | 1500 |
| tcaatgggtc | tcggcaaagc | ctgtgcgctg | atcaccgacg | gtcgtttctc | tggtggcacc | 1560 |
| tctggtcttt | ccatcggcca | cgtctcaccg | gaagcggcaa | gcggcggcag | cattggcctg | 1620 |
| attgaagatg | gtgacctgat | cgctatcgac | atcccgaacc | gtggcattca | gttacaggta | 1680 |
| agcgatgccg | aactggcggc | gcgtcgtgaa | gcgcaggacg | ctcgaggtga | caaagcctgg | 1740 |
| acgccgaaaa | atcgtgaacg | tcaggtctcc | tttgccctgc | gtgcttatgc | cagcctggca | 1800 |
| accagcgccg | acaaaggcgc | ggtgcgcgat | aaatcgaaac | tggggggtta | a | 1851 |

```
<210> SEQ ID NO 6
<211> LENGTH: 616
<212> TYPE: PRT
<213> ORGANISM: E. coli

<400> SEQUENCE: 6
```

| | | | | | | | | | | | | | | |
|---|---|---|---|---|---|---|---|---|---|---|---|---|---|---|
| Met | Pro | Lys | Tyr | Arg | Ser | Ala | Thr | Thr | Thr | His | Gly | Arg | Asn | Met | Ala |
| 1 | | | | 5 | | | | | 10 | | | | | 15 | |
| Gly | Ala | Arg | Ala | Leu | Trp | Arg | Ala | Thr | Gly | Met | Thr | Asp | Ala | Asp | Phe |
| | | | 20 | | | | | 25 | | | | | 30 | | |
| Gly | Lys | Pro | Ile | Ile | Ala | Val | Val | Asn | Ser | Phe | Thr | Gln | Phe | Val | Pro |
| | | 35 | | | | | 40 | | | | | 45 | | | |
| Gly | His | Val | His | Leu | Arg | Asp | Leu | Gly | Lys | Leu | Val | Ala | Glu | Gln | Ile |
| | 50 | | | | | 55 | | | | | 60 | | | | |
| Glu | Ala | Ala | Gly | Gly | Val | Ala | Lys | Glu | Phe | Asn | Thr | Ile | Ala | Val | Asp |
| 65 | | | | | 70 | | | | | 75 | | | | | 80 |
| Asp | Gly | Ile | Ala | Met | Gly | His | Gly | Gly | Met | Leu | Tyr | Ser | Leu | Pro | Ser |
| | | | | 85 | | | | | 90 | | | | | 95 | |
| Arg | Glu | Leu | Ile | Ala | Asp | Ser | Val | Glu | Tyr | Met | Val | Asn | Ala | His | Cys |
| | | | 100 | | | | | 105 | | | | | 110 | | |
| Ala | Asp | Ala | Met | Val | Cys | Ile | Ser | Asn | Cys | Asp | Lys | Ile | Thr | Pro | Gly |
| | | 115 | | | | | 120 | | | | | 125 | | | |
| Met | Leu | Met | Ala | Ser | Leu | Arg | Leu | Asn | Ile | Pro | Val | Ile | Phe | Val | Ser |
| | 130 | | | | | 135 | | | | | 140 | | | | |
| Gly | Gly | Pro | Met | Glu | Ala | Gly | Lys | Thr | Lys | Leu | Ser | Asp | Gln | Ile | Ile |
| 145 | | | | | 150 | | | | | 155 | | | | | 160 |
| Lys | Leu | Asp | Leu | Val | Asp | Ala | Met | Ile | Gln | Gly | Ala | Asp | Pro | Lys | Val |
| | | | | 165 | | | | | 170 | | | | | 175 | |
| Ser | Asp | Ser | Gln | Ser | Asp | Gln | Val | Glu | Arg | Ser | Ala | Cys | Pro | Thr | Cys |
| | | | 180 | | | | | 185 | | | | | 190 | | |
| Gly | Ser | Cys | Ser | Gly | Met | Phe | Thr | Ala | Asn | Ser | Met | Asn | Cys | Leu | Thr |
| | | 195 | | | | | 200 | | | | | 205 | | | |
| Glu | Ala | Leu | Gly | Leu | Ser | Gln | Pro | Gly | Asn | Gly | Ser | Leu | Leu | Ala | Thr |
| | 210 | | | | | 215 | | | | | 220 | | | | |
| His | Ala | Asp | Arg | Lys | Gln | Leu | Phe | Leu | Asn | Ala | Gly | Lys | Arg | Ile | Val |
| 225 | | | | | 230 | | | | | 235 | | | | | 240 |
| Glu | Leu | Thr | Lys | Arg | Tyr | Tyr | Glu | Gln | Asn | Asp | Glu | Ser | Ala | Leu | Pro |
| | | | | 245 | | | | | 250 | | | | | 255 | |
| Arg | Asn | Ile | Ala | Ser | Lys | Ala | Ala | Phe | Glu | Asn | Ala | Met | Thr | Leu | Asp |
| | | | 260 | | | | | 265 | | | | | 270 | | |
| Ile | Ala | Met | Gly | Gly | Ser | Thr | Asn | Thr | Val | Leu | His | Leu | Leu | Ala | Ala |
| | | 275 | | | | | 280 | | | | | 285 | | | |
| Ala | Gln | Glu | Ala | Glu | Ile | Asp | Phe | Thr | Met | Ser | Asp | Ile | Asp | Lys | Leu |
| | 290 | | | | | 295 | | | | | 300 | | | | |
| Ser | Arg | Lys | Val | Pro | Gln | Leu | Cys | Lys | Val | Ala | Pro | Ser | Thr | Gln | Lys |
| 305 | | | | | 310 | | | | | 315 | | | | | 320 |
| Tyr | His | Met | Glu | Asp | Val | His | Arg | Ala | Gly | Gly | Val | Ile | Gly | Ile | Leu |
| | | | | 325 | | | | | 330 | | | | | 335 | |
| Gly | Glu | Leu | Asp | Arg | Ala | Gly | Leu | Leu | Asn | Arg | Asp | Val | Lys | Asn | Val |
| | | | 340 | | | | | 345 | | | | | 350 | | |
| Leu | Gly | Leu | Thr | Leu | Pro | Gln | Thr | Leu | Glu | Gln | Tyr | Asp | Val | Met | Leu |
| | | 355 | | | | | 360 | | | | | 365 | | | |
| Thr | Gln | Asp | Asp | Ala | Val | Lys | Asn | Met | Phe | Arg | Ala | Gly | Pro | Ala | Gly |

```
                    370                375               380
Ile Arg Thr Thr Gln Ala Phe Ser Gln Asp Cys Arg Trp Asp Thr Leu
385                390                      395                400

Asp Asp Asp Arg Ala Asn Gly Cys Ile Arg Ser Leu Glu His Ala Tyr
                 405                410                 415

Ser Lys Asp Gly Gly Leu Ala Val Leu Tyr Gly Asn Phe Ala Glu Asn
            420                 425                430

Gly Cys Ile Val Lys Thr Ala Gly Val Asp Asp Ser Ile Leu Lys Phe
                435                 440                445

Thr Gly Pro Ala Lys Val Tyr Glu Ser Gln Asp Asp Ala Val Glu Ala
            450                 455                460

Ile Leu Gly Gly Lys Val Val Ala Gly Asp Val Val Ile Arg Tyr
465                 470                475                480

Glu Gly Pro Lys Gly Gly Pro Gly Met Gln Glu Met Leu Tyr Pro Thr
                485                 490                495

Ser Phe Leu Lys Ser Met Gly Leu Gly Lys Ala Cys Ala Leu Ile Thr
            500                 505                510

Asp Gly Arg Phe Ser Gly Gly Thr Ser Gly Leu Ser Ile Gly His Val
                515                 520                525

Ser Pro Glu Ala Ala Ser Gly Ser Ile Gly Leu Ile Glu Asp Gly
            530                 535                540

Asp Leu Ile Ala Ile Asp Ile Pro Asn Arg Gly Ile Gln Leu Gln Val
545                 550                555                560

Ser Asp Ala Glu Leu Ala Ala Arg Arg Glu Ala Gln Asp Ala Arg Gly
                565                 570                575

Asp Lys Ala Trp Thr Pro Lys Asn Arg Glu Arg Gln Val Ser Phe Ala
                580                 585                590

Leu Arg Ala Tyr Ala Ser Leu Ala Thr Ser Ala Asp Lys Gly Ala Val
                595                 600                605

Arg Asp Lys Ser Lys Leu Gly Gly
            610                 615

<210> SEQ ID NO 7
<211> LENGTH: 1662
<212> TYPE: DNA
<213> ORGANISM: Lactococcus lactis

<400> SEQUENCE: 7
tctagacata tgtatactgt gggggattac ctgctggatc gcctgcacga actgggatt      60 gaagaaattt tcggtgtgcc aggcgattat aacctgcagt cctggaccaa gattatctcg    120
cacaaagata tgaagtgggt cggtaacgcc aacgaactga acgcgagcta tggcagat     180 ggttatgccc gtaccaaaaa agctgctgcg tttctgacga cctttggcgt tggcgaactg    240
agcgccgtca acggactggc aggaagctac gccgagaacc tgccagttgt cgaaattgtt    300
gggtcgccta cttctaaggt tcagaatgaa ggcaaatttg tgcaccatac tctggctgat    360
ggggatttta acatttttat gaaaatgcat gaaccggtta ctgcggcccg cacgctgctg    420
acagcagaga atgctacggt tgagatcgac cgcgtcctgt ctgcgctgct gaaagagcgc    480
aagccggtat atatcaatct gcctgtcgat gttgccgcag cgaaagccga aaagccgtcg    540
ctgccactga aaaagaaaa cagcacctcc aatacatcgg accaggaaat tctgaataaa    600
atccaggaat cactgaagaa tgcgaagaaa ccgatcgtca tcaccggaca tgagatcatc    660
tcttttggcc tggaaaaaac ggtcacgcag ttcatttcta agaccaaact gcctatcacc    720
```

```
accctgaact tcggcaaatc tagcgtcgat gaagcgctgc cgagttttct gggtatctat    780
aatggtaccc tgtccgaacc gaacctgaaa gaattcgtcg aaagcgcgga ctttatcctg    840
atgctgggcg tgaaactgac ggatagctcc acaggcgcat tacccacca tctgaacgag    900 aataaaatga tttccctgaa tatcgacgaa ggcaaaatct ttaacgagcg catccagaac    960
ttcgattttg aatctctgat tagttcgctg ctggatctgt ccgaaattga gtataaaggt   1020
aaatatattg ataaaaaaca ggaggatttt gtgccgtcta atgcgctgct gagtcaggat   1080
cgtctgtggc aagccgtaga aaacctgaca cagtctaatg aaacgattgt tgcggaacag   1140
ggaacttcat ttttcggcgc ctcatccatt tttctgaaat ccaaaagcca tttcattggc   1200
caaccgctgt gggggagtat tggttatacc tttccggcgg cgctgggttc acagattgca   1260
gataaggaat cacgccatct gctgtttatt ggtgacggca gcctgcagct gactgtccag   1320
gaactggggc tggcgatccg tgaaaaaatc aatccgattt gctttatcat caataacgac   1380
ggctacaccg tcgaacgcga aattcatgga ccgaatcaaa gttacaatga catcccgatg   1440
tggaactata gcaaactgcc ggaatccttt ggcgcgacag aggatcgcgt ggtgagtaaa   1500
attgtgcgta cggaaaacga atttgtgtcg gttatgaaag aagcgcaggc tgacccgaat   1560
cgcatgtatt ggattgaact gatcctggca aagaaggcg caccgaaagt tctgaaaaag   1620
atggggaaac tgtttgcgga gcaaaataaa agctaaggat cc                     1662
```

<210> SEQ ID NO 8
<211> LENGTH: 548
<212> TYPE: PRT
<213> ORGANISM: Lactococcus lactis

<400> SEQUENCE: 8

```
Met Tyr Thr Val Gly Asp Tyr Leu Leu Asp Arg Leu His Glu Leu Gly
1               5                  10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205
```

Ile Val Ile Thr Gly His Glu Ile Ile Ser Phe Gly Leu Glu Lys Thr
210              215                 220

Val Thr Gln Phe Ile Ser Lys Thr Lys Leu Pro Ile Thr Thr Leu Asn
225              230                 235                 240

Phe Gly Lys Ser Ser Val Asp Glu Ala Leu Pro Ser Phe Leu Gly Ile
                 245                 250                 255

Tyr Asn Gly Thr Leu Ser Glu Pro Asn Leu Lys Glu Phe Val Glu Ser
                 260                 265                 270

Ala Asp Phe Ile Leu Met Leu Gly Val Lys Leu Thr Asp Ser Ser Thr
            275                 280                 285

Gly Ala Phe Thr His His Leu Asn Glu Asn Lys Met Ile Ser Leu Asn
290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
                340                 345                 350

Leu Leu Ser Gln Asp Arg Leu Trp Gln Ala Val Glu Asn Leu Thr Gln
            355                 360                 365

Ser Asn Glu Thr Ile Val Ala Glu Gln Gly Thr Ser Phe Phe Gly Ala
370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
            450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
                500                 505                 510

Gln Ala Asp Pro Asn Arg Met Tyr Trp Ile Glu Leu Ile Leu Ala Lys
            515                 520                 525

Glu Gly Ala Pro Lys Val Leu Lys Lys Met Gly Lys Leu Phe Ala Glu
530                 535                 540

Gln Asn Lys Ser
545

<210> SEQ ID NO 9
<211> LENGTH: 1164
<212> TYPE: DNA
<213> ORGANISM: E. coli

<400> SEQUENCE: 9
atgaacaact ttaatctgca cacccccaacc cgcattctgt ttggtaaagg cgcaatcgct    60
ggtttacgcg aacaaattcc tcacgatgct cgcgtattga ttacctacgg cggcggcagc   120
gtgaaaaaaa ccggcgttct cgatcaagtt ctggatgccc tgaaaggcat ggacgtgctg   180

```
gaatttggcg gtattgagcc aaacccggct tatgaaacgc tgatgaacgc cgtgaaactg      240
gttcgcgaac agaaagtgac tttcctgctg gcggttggcg gcggttctgt actggacggc      300
accaaattta tcgccgcagc ggctaactat ccggaaaata tcgatccgtg cacattctg       360 caaacgggcg gtaaagagat taaaagcgcc atcccgatgg gctgtgtgct gacgctgcca      420
gcaaccggtt cagaatccaa cgcaggcgcg gtgatctccc gtaaaaccac aggcgacaag      480
caggcgttcc attctgccca tgttcagccg gtatttgccg tgctcgatcc ggtttatacc      540
tacaccctgc cgccgcgtca ggtggctaac ggcgtagtgg acgcctttgt acacaccgtg      600
gaacagtatg ttaccaaacc ggttgatgcc aaaattcagg accgtttcgc agaaggcatt      660
ttgctgacgc taatcgaaga tggtccgaaa gccctgaaag agccagaaaa ctacgatgtg      720
cgcgccaacg tcatgtgggc ggcgactcag gcgctgaacg gtttgattgg cgctggcgta      780
ccgcaggact gggcaacgca tatgctgggc acgaactga ctgcgatgca cggtctggat       840
cacgcgcaaa cactggctat cgtcctgcct gcactgtgga atgaaaaacg cgataccaag      900
cgcgctaagc tgctgcaata tgctgaacgc gtctggaaca tcactgaagg ttccgatgat      960
gagcgtattg acgccgcgat tgccgcaacc cgcaatttct ttgagcaatt aggcgtgccg     1020
acccacctct ccgactacgg tctggacggc agctccatcc cggctttgct gaaaaaactg     1080
gaagagcacg gcatgaccca actgggcgaa atcatgaca ttacgttgga tgtcagccgc      1140
cgtatatacg aagccgcccg ctaa                                            1164
```

<210> SEQ ID NO 10
<211> LENGTH: 387
<212> TYPE: PRT
<213> ORGANISM: E. coli

<400> SEQUENCE: 10

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190
```

-continued

```
Val Asp Ala Phe Val His Thr Val Glu Gln Tyr Val Thr Lys Pro Val
            195                 200                 205
Asp Ala Lys Ile Gln Asp Arg Phe Ala Glu Gly Ile Leu Leu Thr Leu
210                 215                 220
Ile Glu Asp Gly Pro Lys Ala Leu Lys Glu Pro Glu Asn Tyr Asp Val
225                 230                 235                 240
Arg Ala Asn Val Met Trp Ala Thr Gln Ala Leu Asn Gly Leu Ile
                245                 250                 255
Gly Ala Gly Val Pro Gln Asp Trp Ala Thr His Met Leu Gly His Glu
                260                 265                 270
Leu Thr Ala Met His Gly Leu Asp His Ala Gln Thr Leu Ala Ile Val
                275                 280                 285
Leu Pro Ala Leu Trp Asn Glu Lys Arg Asp Thr Lys Arg Ala Lys Leu
            290                 295                 300
Leu Gln Tyr Ala Glu Arg Val Trp Asn Ile Thr Glu Gly Ser Asp Asp
305                 310                 315                 320
Glu Arg Ile Asp Ala Ala Ile Ala Ala Thr Arg Asn Phe Phe Glu Gln
                325                 330                 335
Leu Gly Val Pro Thr His Leu Ser Asp Tyr Gly Leu Asp Gly Ser Ser
                340                 345                 350
Ile Pro Ala Leu Leu Lys Lys Leu Glu Glu His Gly Met Thr Gln Leu
                355                 360                 365
Gly Glu Asn His Asp Ile Thr Leu Asp Val Ser Arg Arg Ile Tyr Glu
                370                 375                 380
Ala Ala Arg
385
```

<210> SEQ ID NO 11
<211> LENGTH: 44
<212> TYPE: DNA
<213> ORGANISM: artificial sequence
<220> FEATURE:
<223> OTHER INFORMATION: primer

<400> SEQUENCE: 11
gagctcctta agaaggaggt aatcaccatg gctaactact tcaa        44

<210> SEQ ID NO 12
<211> LENGTH: 51
<212> TYPE: DNA
<213> ORGANISM: artificial sequence
<220> FEATURE:
<223> OTHER INFORMATION: primer

<400> SEQUENCE: 12
ggatccgatc gagctagcgc ggccgcttaa cccgcaacag caatacgttt c        51

<210> SEQ ID NO 13
<211> LENGTH: 35
<212> TYPE: DNA
<213> ORGANISM: artificial sequence
<220> FEATURE:
<223> OTHER INFORMATION: primer

<400> SEQUENCE: 13
gctaacagga ggaagagctc atggcaccct cgctc        35

<210> SEQ ID NO 14
<211> LENGTH: 35
<212> TYPE: DNA

<213> ORGANISM: artificial sequence
<220> FEATURE:
<223> OTHER INFORMATION: primer

<400> SEQUENCE: 14
gagcgagggt gccatgagct cttcctcctg ttagc             35

<210> SEQ ID NO 15
<211> LENGTH: 44
<212> TYPE: DNA
<213> ORGANISM: artificial sequence
<220> FEATURE:
<223> OTHER INFORMATION: primer

<400> SEQUENCE: 15
atcaccgagc tcatggctaa ctacttcaat acactgaatc tgcg             44

<210> SEQ ID NO 16
<211> LENGTH: 46
<212> TYPE: DNA
<213> ORGANISM: artificial sequence
<220> FEATURE:
<223> OTHER INFORMATION: primer

<400> SEQUENCE: 16
ggccgcaagc ttttaacccg caacagcaat acgtttcata tctgtc             46

<210> SEQ ID NO 17
<211> LENGTH: 20
<212> TYPE: DNA
<213> ORGANISM: artificial sequence
<220> FEATURE:
<223> OTHER INFORMATION: primer

<400> SEQUENCE: 17
ccgtaaagat atcaccgtag             20

<210> SEQ ID NO 18
<211> LENGTH: 20
<212> TYPE: DNA
<213> ORGANISM: artificial sequence
<220> FEATURE:
<223> OTHER INFORMATION: primer

<400> SEQUENCE: 18
cagtatgaag gcaaaatcgg             20

<210> SEQ ID NO 19
<211> LENGTH: 20
<212> TYPE: DNA
<213> ORGANISM: artificial sequence
<220> FEATURE:
<223> OTHER INFORMATION: primer

<400> SEQUENCE: 19
cgtactcagc ggtatcagag             20

<210> SEQ ID NO 20
<211> LENGTH: 20
<212> TYPE: DNA
<213> ORGANISM: artificial sequence
<220> FEATURE:
<223> OTHER INFORMATION: primer

<400> SEQUENCE: 20
cagatttcac ttccgcaacg             20

<210> SEQ ID NO 21
<211> LENGTH: 29
<212> TYPE: DNA
<213> ORGANISM: artificial sequence
<220> FEATURE:
<223> OTHER INFORMATION: primer

<400> SEQUENCE: 21
cgcaactctc tactgtttct ccatacccg                              29

<210> SEQ ID NO 22
<211> LENGTH: 25
<212> TYPE: DNA
<213> ORGANISM: artificial sequence
<220> FEATURE:
<223> OTHER INFORMATION: primer

<400> SEQUENCE: 22
accgcttctg cgttctgatt taatc                                  25

<210> SEQ ID NO 23
<211> LENGTH: 44
<212> TYPE: DNA
<213> ORGANISM: artificial sequence
<220> FEATURE:
<223> OTHER INFORMATION: primer

<400> SEQUENCE: 23
caaaacagcc aagctttag ttcttgctct tgtcgacgat cttg              44

<210> SEQ ID NO 24
<211> LENGTH: 43
<212> TYPE: DNA
<213> ORGANISM: artificial sequence
<220> FEATURE:
<223> OTHER INFORMATION: primer

<400> SEQUENCE: 24
caggaggaag agctcatgcg cgttttctac gataaagact gtg              43

<210> SEQ ID NO 25
<211> LENGTH: 44
<212> TYPE: DNA
<213> ORGANISM: artificial sequence
<220> FEATURE:
<223> OTHER INFORMATION: primer

<400> SEQUENCE: 25
caaaacagcc aagctttag ttcttggctt tgtcgacgat tttg              44

<210> SEQ ID NO 26
<211> LENGTH: 45
<212> TYPE: DNA
<213> ORGANISM: artificial sequence
<220> FEATURE:
<223> OTHER INFORMATION: primer

<400> SEQUENCE: 26
caggaggaag agctcatgaa agttttctac gataaagact gcgac            45

<210> SEQ ID NO 27
<211> LENGTH: 20
<212> TYPE: DNA
<213> ORGANISM: artificial sequence
<220> FEATURE:

<223> OTHER INFORMATION: primer

<400> SEQUENCE: 27
gatcatgatc gcgccgaagg                                                   20

<210> SEQ ID NO 28
<211> LENGTH: 20
<212> TYPE: DNA
<213> ORGANISM: artificial sequence
<220> FEATURE:
<223> OTHER INFORMATION: primer

<400> SEQUENCE: 28
ctgctcaccg aacaggtcgg                                                   20

<210> SEQ ID NO 29
<211> LENGTH: 1476
<212> TYPE: DNA
<213> ORGANISM: E. coli

<400> SEQUENCE: 29
atggctaact acttcaatac actgaatctg cgccagcagc tggcacagct gggcaaatgt        60
cgctttatgg gccgcgatga attcgccgat ggcgcgagct accttcaggg taaaaaagta      120
gtcatcgtcg gctgtggcgc acagggtctg aaccagggcc tgaacatgcg tgattctggt      180
ctcgatatct cctacgctct gcgtaaagaa gcgattgccg agaagcgcgc gtcctggcgt      240
aaagcgaccg aaaatggttt taaagtgggt acttacgaag aactgatccc acaggcggat      300
ctggtgatta acctgacgcc ggacaagcag cactctgatg tagtgcgcac cgtacagcca      360
ctgatgaaag acggcgcggc gctgggctac tcgcacggtt tcaacatcgt cgaagtgggc      420
gagcagatcc gtaaagatat caccgtagtg atggttgcgc cgaaatgccc aggcaccgaa      480
gtgcgtgaag agtacaaacg tgggttcggc gtaccgacgc tgattgccgt tcacccggaa      540
aacgatccga aggcgaagg catggcgatt gccaaagcct gggcggctgc aaccggtggt      600
caccgtgcgg gtgtgctgga atcgtccttc gttgcggaag tgaaatctga cctgatgggc      660
gagcaaacca tcctgtgcgg tatgttgcag gctggctctc tgctgtgctt cgacaagctg      720
gtggaagaag gtaccgatcc agcatacgca gaaaaactga ttcagttcgg ttgggaaacc      780
atcaccgaag cactgaaaca gggcggcatc accctgatga tggaccgtct ctctaacccg      840
gcgaaactgc gtgcttatgc gctttctgaa cagctgaaag atcatggc accctgttc      900
cagaaacata tggacgacat catctccggc gaattctctt ccggtatgat ggcggactgg      960
gccaacgatg ataagaaact gctgacctgg cgtgaagaga ccggcaaaac cgcgtttgaa     1020
accgcgccgc agtatgaagg caaaatcggc gagcaggagt acttcgataa aggcgtactg     1080
atgattgcga tggtgaaagc gggcgttgaa ctggcgttcg aaaccatggt cgattccggc     1140
atcattgaag agtctgcata ttatgaatca ctgcacgagc tgccgctgat tgccaacacc     1200
atcgcccgta agcgtctgta cgaaatgaac gtggttatct ctgataccgc tgagtacggt     1260
aactatctgt tctcttacgc ttgtgtgccg ttgctgaaac cgtttatggc agagctgcaa     1320
ccgggcgacc tgggtaaagc tattccgaa ggcgcggtag ataacgggca actgcgtgat     1380
gtgaacgaag cgattcgcag ccatgcgatt gagcaggtag gtaagaaact gcgcggctat     1440
atgacagata tgaaacgtat tgctgttgcg ggttaa                               1476

<210> SEQ ID NO 30
<211> LENGTH: 1485

<212> TYPE: DNA
<213> ORGANISM: Artificial sequence
<220> FEATURE:
<223> OTHER INFORMATION: codon-optimized V. cholerae VC0162 gene

<400> SEQUENCE: 30
atggctaact attttaacac tctgaatctg cgcgaacagc tggatcagct gggtcgttgt 60
cgcttcatgg cgcgcgagga attcgcaact gaagcggact acctgaaggg taagaaagtg 120
gtcatcgtag gctgtggcgc gcagggcctg aaccagggtc tgaatatgcg tgatagcggc 180
ctggacgtgt cttacgcact gcgtcaagcg gccatcgatg aacagcgtca gtctttcaaa 240
aatgctaaga acaacggttt caatgtaggt tcttacgaac agctgattcc gacggcggac 300
ctggttatca atctgacccc ggataaacag cacaccagcg tggttaacgc ggttatgccg 360
ctgatgaaac agggcgctgc tctgggctat agccatggtt ttaacatcgt ggaagagggc 420
atgcagattc gtaaagacat cacggtagta atggtggcgc cgaaatgccc aggtactgag 480
gttcgtgagg aatacaagcg tggttttggc gttcctaccc tgattgcagt gcacccggaa 540
aacgatccgc agggcgaagg ttgggaaatc gctaaggcat gggctgcagc cactggtggc 600
caccgcgctg gttgcctggc ctctagcttc gtcgcagaag taaaaagcga cctgatgggc 660
gaacagacca tcctgtgtgg tatgctgcag gccggtagca tcgtttgcta cgaaaagatg 720
gttgctgatg gtatcgaccc gggctacgcg ggcaaactgc tgcagtttgg ttgggaaact 780
attaccgagg ctctgaaatt cggtggcatc acccacatga tggaccgtct gagcaacccg 840
gcaaagatca aagcattcga actgtctgaa gagctgaaag acctgatgcg tccgctgtac 900
aacaagcaca tggacgacat tatttccggc cacttttctt ctaccatgat ggcggactgg 960
gccaacgacg acaaggatct gttcggctgg cgtgcggaga ccgctgaaac cgcatttgaa 1020
aactatccga ccactgacgt taagatcgcg gagcaggaat actttgacaa cggtatcctg 1080
atgattgcaa tggttcgcgc gggcgttgaa ctggcgtttg aagcgatgac cgcttctggt 1140
atcatcgatg aatctgcata ctatgagtcc ctgcacgagc tgccgctgat cgctaacacg 1200
gtggcccgca aacgtctgta tgaaatgaat gtcgtaatct ctgacacggc tgaatatggt 1260
aattatctgt tcgccaatgt ggcagttcct ctgctgcgtg agaaattcat gccgaaagtg 1320
ggtaccgatg ttattggtaa aggtctgggt gtcgtttcta accaggtaga taacgcgact 1380
ctgatcgaag tgaactccat catccgtaac cacccggtgg aatacattgg tgaagaactg 1440
cgtggttata tgaaggacat gaagcgtatc gccgttggtg attaa 1485

<210> SEQ ID NO 31
<211> LENGTH: 1014
<212> TYPE: DNA
<213> ORGANISM: Pseudomonas aeruginosa

<400> SEQUENCE: 31
atgcgcgttt tctacgataa agactgtgac ctctcgatca tccagggcaa gaaagttgcc 60
atcatcggct acggctccca gggccacgcc catgcctgca acctgaagga ctccggcgtc 120
gacgtcaccg tgggcctgcg tagcggctcc gccaccgtgg ccaaggccga agcgcacggt 180
ctgaaggttg ccgacgtgaa gaccgccgtc gccgcagccg acgtggtcat gatcctcacc 240
ccggacgagt tccagggccg cctgtacaag gaagagatcg agccgaacct gaagaagggc 300
gccaccctgg ccttcgctca cggcttctcc atccactaca accaggtcgt cccgcgcgcc 360
gacctcgacg tgatcatgat cgcgccgaag gcaccgggtc acaccgtgcg ttccgagttc 420

```
gtcaagggcg gtggcatccc tgacctgatc gccatctacc aggacgcttc cggcaacgcc      480
aagaacgtcg ccctgtccta cgcctgcggc gtcggcggcg tcgtaccgg  tatcatcgaa      540 accaccttca aggacgagac cgaaaccgac ctgttcggtg agcaggccgt tctctgcggt      600
ggttgcgtcg agctggtcaa ggccggtttc gaaaccctgg tcgaagccgg ttacgcgccg      660
gaaatggcct acttcgagtg cctgcacgag ctgaagctga tcgtcgacct gatgtacgaa      720
ggcggcatcg ccaacatgaa ctactccatc tccaacaatg ccgaatacgg tgagtacgta      780
accggtccgg aggtgatcaa cgccgagtcc cgtgctgcca tgcgcaacgc cctgaagcgc      840
atccaggacg gcgagtacgc gaaaatgttc attaccgaag gtgcggccaa ctacccgtcg      900
atgactgcct accgccgcaa caacgccgct cacccgatcg agcagatcgg cgagaagctg      960
cgcgcgatga tgccgtggat cgcagccaac aagatcgtcg acaagagcaa gaac          1014
```

<210> SEQ ID NO 32
<211> LENGTH: 1014
<212> TYPE: DNA
<213> ORGANISM: Pseudomonas fluorescens

<400> SEQUENCE: 32

```
atgaaagttt tctacgataa agactgcgac ctgtcgatca tccaaggtaa gaaagttgcc       60
atcatcggct acggttccca gggccacgct caagcatgca acctgaagga ttccggcgta      120
gacgtgactg ttggcctgcg taaaggctcg gctaccgttg ccaaggctga agcccacggc      180
ttgaaagtga ccgacgttgc tgcagccgtt gccggtgccg acttggtcat gatcctgacc      240
ccggacgagt tccagtccca gctgtacaag aacgaaatcg agccgaacat caagaagggc      300
gccactctgg ccttctccca cggcttcgcg atccactaca accaggttgt gcctcgtgcc      360
gacctcgacg tgatcatgat cgcgccgaag gctccaggcc acaccgtacg ttccgagttc      420
gtcaagggcg gtggtattcc tgacctgatc gcgatctacc aggacgcttc cggcaacgcc      480
aagaacgttg ccctgtccta cgccgcaggc gtgggcggcg ccgtaccgg  catcatcgaa      540 accaccttca aggacgagac tgaaaccgac ctgttcggtg agcaggctgt tctgtgtggc      600
ggtaccgtcg agctggtcaa agccggtttc gaaaccctgg ttgaagctgg ctacgctcca      660
gaaatggcct acttcgagtg cctgcacgaa ctgaagctga tcgttgacct catgtacgaa      720
ggcggtatcg ccaacatgaa ctactcgatc tccaacaacg ctgaatacgg cgagtacgtg      780
actggtccag aagtcatcaa cgccgaatcc cgtcaggcca tgcgcaatgc tctgaagcgc      840
atccaggacg gcgaatacgc gaagatgttc atcagcgaag cgctaccgg  ctacccatcg      900 atgaccgcca agcgtcgtaa caacgctgct cacggtatcg aaatcatcgg cgagcaactg      960
cgctcgatga tgccttggat cggtgccaac aaaatcgtcg acaaagccaa gaac          1014
```

<210> SEQ ID NO 33
<211> LENGTH: 491
<212> TYPE: PRT
<213> ORGANISM: E. coli

<400> SEQUENCE: 33

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
                20                  25                  30

Ser Tyr Leu Gln Gly Lys Lys Val Val Ile Val Gly Cys Gly Ala Gln
            35                  40                  45

```
Gly Leu Asn Gln Gly Leu Asn Met Arg Asp Ser Gly Leu Asp Ile Ser
     50                  55                  60

Tyr Ala Leu Arg Lys Glu Ala Ile Ala Glu Lys Arg Ala Ser Trp Arg
 65                  70                  75                  80

Lys Ala Thr Glu Asn Gly Phe Lys Val Gly Thr Tyr Glu Glu Leu Ile
                 85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
```

```
                465                 470                 475                 480
Met Thr Asp Met Lys Arg Ile Ala Val Ala Gly
                485                 490

<210> SEQ ID NO 34
<211> LENGTH: 494
<212> TYPE: PRT
<213> ORGANISM: Vibrio cholerae

<400> SEQUENCE: 34

Met Ala Asn Tyr Phe Asn Thr Leu Asn Leu Arg Glu Gln Leu Asp Gln
1               5                   10                  15

Leu Gly Arg Cys Arg Phe Met Ala Arg Glu Glu Phe Ala Thr Glu Ala
            20                  25                  30

Asp Tyr Leu Lys Gly Lys Lys Val Ile Val Gly Cys Gly Ala Gln
        35                  40                  45

Gly Leu Asn Gln Gly Leu Asn Met Arg Asp Ser Gly Leu Asp Val Ser
    50                  55                  60

Tyr Ala Leu Arg Gln Ala Ala Ile Asp Glu Gln Arg Gln Ser Phe Lys
65                  70                  75                  80

Asn Ala Lys Asn Asn Gly Phe Asn Val Gly Ser Tyr Glu Gln Leu Ile
                85                  90                  95

Pro Thr Ala Asp Leu Val Ile Asn Leu Thr Pro Asp Lys Gln His Thr
            100                 105                 110

Ser Val Val Asn Ala Val Met Pro Leu Met Lys Gln Gly Ala Ala Leu
        115                 120                 125

Gly Tyr Ser His Gly Phe Asn Ile Val Glu Glu Gly Met Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Gln Gly Glu Gly Trp Glu Ile Ala Lys
            180                 185                 190

Ala Trp Ala Ala Ala Thr Gly Gly His Arg Ala Gly Cys Leu Ala Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Ile Val Cys Tyr Glu Lys Met
225                 230                 235                 240

Val Ala Asp Gly Ile Asp Pro Gly Tyr Ala Gly Lys Leu Leu Gln Phe
                245                 250                 255

Gly Trp Glu Thr Ile Thr Glu Ala Leu Lys Phe Gly Gly Ile Thr His
            260                 265                 270

Met Met Asp Arg Leu Ser Asn Pro Ala Lys Ile Lys Ala Phe Glu Leu
        275                 280                 285

Ser Glu Glu Leu Lys Asp Leu Met Arg Pro Leu Tyr Asn Lys His Met
    290                 295                 300

Asp Asp Ile Ile Ser Gly His Phe Ser Ser Thr Met Met Ala Asp Trp
305                 310                 315                 320

Ala Asn Asp Asp Lys Asp Leu Phe Gly Trp Arg Ala Glu Thr Ala Glu
                325                 330                 335

Thr Ala Phe Glu Asn Tyr Pro Thr Thr Asp Val Lys Ile Ala Glu Gln
            340                 345                 350
```

```
Glu Tyr Phe Asp Asn Gly Ile Leu Met Ile Ala Met Val Arg Ala Gly
            355                 360                 365

Val Glu Leu Ala Phe Glu Ala Met Thr Ala Ser Gly Ile Ile Asp Glu
    370                 375                 380

Ser Ala Tyr Tyr Glu Ser Leu His Glu Leu Pro Leu Ile Ala Asn Thr
385                 390                 395                 400

Val Ala Arg Lys Arg Leu Tyr Glu Met Asn Val Val Ile Ser Asp Thr
                405                 410                 415

Ala Glu Tyr Gly Asn Tyr Leu Phe Ala Asn Val Ala Val Pro Leu Leu
                420                 425                 430

Arg Glu Lys Phe Met Pro Lys Val Gly Thr Asp Val Ile Gly Lys Gly
            435                 440                 445

Leu Gly Val Val Ser Asn Gln Val Asp Asn Ala Thr Leu Ile Glu Val
    450                 455                 460

Asn Ser Ile Ile Arg Asn His Pro Val Glu Tyr Ile Gly Glu Glu Leu
465                 470                 475                 480

Arg Gly Tyr Met Lys Asp Met Lys Arg Ile Ala Val Gly Asp
                485                 490

<210> SEQ ID NO 35
<211> LENGTH: 338
<212> TYPE: PRT
<213> ORGANISM: Pseudomonas aeruginosa

<400> SEQUENCE: 35

Met Arg Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala His Ala
            20                  25                  30

Cys Asn Leu Lys Asp Ser Gly Val Asp Val Thr Val Gly Leu Arg Ser
        35                  40                  45

Gly Ser Ala Thr Val Ala Lys Ala Glu Ala His Gly Leu Lys Val Ala
    50                  55                  60

Asp Val Lys Thr Ala Val Ala Ala Asp Val Val Met Ile Leu Thr
65                  70                  75                  80

Pro Asp Glu Phe Gln Gly Arg Leu Tyr Lys Glu Ile Glu Pro Asn
                85                  90                  95

Leu Lys Lys Gly Ala Thr Leu Ala Phe Ala His Gly Phe Ser Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Cys Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Cys Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240
```

-continued

```
Gly Gly Ile Ala Asn Met Asn Tyr Ser Ile Ser Asn Ala Glu Tyr
            245                 250                 255

Gly Glu Tyr Val Thr Gly Pro Glu Val Ile Asn Ala Glu Ser Arg Ala
            260                 265                 270

Ala Met Arg Asn Ala Leu Lys Arg Ile Gln Asp Gly Tyr Ala Lys
            275                 280                 285

Met Phe Ile Thr Glu Gly Ala Ala Asn Tyr Pro Ser Met Thr Ala Tyr
    290                 295                 300

Arg Arg Asn Asn Ala Ala His Pro Ile Glu Gln Ile Gly Glu Lys Leu
305                 310                 315                 320

Arg Ala Met Met Pro Trp Ile Ala Asn Lys Ile Val Asp Lys Ser
                325                 330                 335

Lys Asn

<210> SEQ ID NO 36
<211> LENGTH: 338
<212> TYPE: PRT
<213> ORGANISM: Pseudomonas fluorescens

<400> SEQUENCE: 36

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
                20                  25                  30

Cys Asn Leu Lys Asp Ser Gly Val Asp Val Thr Val Gly Leu Arg Lys
            35                  40                  45

Gly Ser Ala Thr Val Ala Lys Ala Glu Ala His Gly Leu Lys Val Thr
        50                  55                  60

Asp Val Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Ala Glu Tyr
                245                 250                 255
```

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
            275                 280                 285

Met Phe Ile Ser Glu Gly Ala Thr Gly Tyr Pro Ser Met Thr Ala Lys
            290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                    325                 330                 335

Lys Asn

<210> SEQ ID NO 37
<211> LENGTH: 63
<212> TYPE: DNA
<213> ORGANISM: artificial sequence
<220> FEATURE:
<223> OTHER INFORMATION: forward primer PAL-F1

<400> SEQUENCE: 37
ctgcagcaca tgaagactcc atggcaccct cgctcgactc gatctcgcac tcgttcgcaa      60
acg                                                                   63

<210> SEQ ID NO 38
<211> LENGTH: 40
<212> TYPE: DNA
<213> ORGANISM: artificial sequence
<220> FEATURE:
<223> OTHER INFORMATION: reverse primer PAL-R1

<400> SEQUENCE: 38
tctctcatcc gccaaaacag aagcttctaa gcgagcatct                            40

<210> SEQ ID NO 39
<211> LENGTH: 43
<212> TYPE: DNA
<213> ORGANISM: artificial sequence
<220> FEATURE:
<223> OTHER INFORMATION: primer PAL-EcoRI-F1

<400> SEQUENCE: 39
gggctaacag gaggaagaat tcatggcacc ctcgctcgac tcg                        43

<210> SEQ ID NO 40
<211> LENGTH: 42
<212> TYPE: DNA
<213> ORGANISM: artificial sequence
<220> FEATURE:
<223> OTHER INFORMATION: reverse primer PAL-EcoRI-R1

<400> SEQUENCE: 40
cgagtcgagc gagggtgcca tgaattcttc ctcctgtagc cc                         42